US012605562B2

(12) United States Patent
Marsteller et al.

(10) Patent No.: US 12,605,562 B2
(45) Date of Patent: *Apr. 21, 2026

(54) OPHTHALMIC BRACHYTHERAPY SYSTEMS AND DEVICES FOR APPLICATION OF BETA RADIATION

(71) Applicant: RADIANCE THERAPEUTICS, INC., Tucson, AZ (US)

(72) Inventors: Laurence J. Marsteller, Tucson, AZ (US); James A. Fazio, Tucson, AZ (US); Ian Murdoch, Tucson, AZ (US)

(73) Assignee: RADIANCE THERAPEUTICS, INC., Tucson, AZ (US)

( * ) Notice: Subject to any disclaimer, the term of this patent is extended or adjusted under 35 U.S.C. 154(b) by 1014 days.

This patent is subject to a terminal disclaimer.

(21) Appl. No.: 17/694,366

(22) Filed: Mar. 14, 2022

(65) Prior Publication Data

US 2022/0212032 A1 Jul. 7, 2022

Related U.S. Application Data

(63) Continuation-in-part of application No. 17/676,711, filed on Feb. 21, 2022, which is a continuation-in-part
(Continued)

(30) Foreign Application Priority Data

Sep. 7, 2017 (GB) ..................................... 1714392

(51) Int. Cl.
*A61N 5/10* (2006.01)

(52) U.S. Cl.
CPC .... *A61N 5/1007* (2013.01); *A61N 2005/1011* (2013.01); *A61N 2005/1024* (2013.01)

(58) Field of Classification Search
CPC .. A61N 5/1001; A61N 5/1007; A61N 5/1014; A61N 5/1017; A61N 2005/1008;
(Continued)

(56) References Cited

U.S. PATENT DOCUMENTS

| | | | |
|---|---|---|---|
| 2,559,793 A | 7/1951 | Pregel | |
| D328,644 S | 8/1992 | Pericic | |

(Continued)

FOREIGN PATENT DOCUMENTS

| | | | |
|---|---|---|---|
| CN | 107995993 A | 5/2018 | |
| EP | 1529554 B1 | 2/2006 | |

(Continued)

OTHER PUBLICATIONS

Kung JS et al: "Cataract Surgery in the Glaucoma Patient", Middle East African Journal of Ophthalmology, vol. 22, No. 1, Mar. 31, 2015 (Mar. 31, 2015), pp. 10-17.
(Continued)

*Primary Examiner* — Carrie R Dorna
(74) *Attorney, Agent, or Firm* — NGUYEN TARBET IP LAW

(57) ABSTRACT

Systems and devices for applying radiation to a target area, for example for maintaining functioning drainage blebs or functioning drainage holes in the eye, e.g., to reduce intraocular pressure (IOP) of an eye being treated for glaucoma. The systems and devices of the present invention provide for the application of beta radiation to the target area, wherein the beta radiation can function to inhibit or reduce the inflammation and/or fibrogenesis that may occur after insertion of an implant into the eye or introduction of a hole for the purpose of draining aqueous humor to maintain a healthy intraocular pressure. By reducing inflamma-
(Continued)

tion and/or fibrogenesis, the implant, the hole, the blebs, or other related structures or tissues can remain functioning appropriately.

20 Claims, 10 Drawing Sheets

Related U.S. Application Data of application No. PCT/US2020/047235, filed on Aug. 20, 2020, application No. 17/694,366 is a continuation-in-part of application No. 16/698,676, filed on Nov. 27, 2019, now Pat. No. 11,273,325, said application No. 17/676,711 is a continuation-in-part of application No. 16/698,676, filed on Nov. 27, 2019, now Pat. No. 11,273,325, application No. 17/694,366 is a continuation-in-part of application No. PCT/US2021/064141, filed on Dec. 17, 2021, said application No. 17/676,711 is a continuation-in-part of application No. PCT/US2021/064141, filed on Dec. 17, 2021, which is a continuation-in-part of application No. PCT/US2021/012694, filed on Jan. 8, 2021, which is a continuation-in-part of application No. PCT/US2021/012744, filed on Jan. 8, 2021, application No. 17/694,366 is a continuation-in-part of application No. PCT/US2021/064190, filed on Dec. 17, 2021, said application No. 17/676,711 is a continuation-in-part of application No. PCT/US2021/064190, filed on Dec. 17, 2021, which is a continuation-in-part of application No. PCT/US2021/012694, filed on Jan. 8, 2021, and a continuation-in-part of application No. PCT/US2021/012744, filed on Jan. 8, 2021, application No. 17/694,366 is a continuation-in-part of application No. PCT/US2020/063435, filed on Dec. 4, 2020, said application No. 17/676,711 is a continuation-in-part of application No. PCT/US2020/063435, filed on Dec. 4, 2020, application No. 17/694,366 is a continuation-in-part of application No. PCT/US2021/012744, filed on Jan. 8, 2021, said application No. 17/676,711 is a continuation-in-part of application No. PCT/US2021/012744, filed on Jan. 8, 2021, application No. 17/694, 366 is a continuation-in-part of application No. PCT/US2021/012694, filed on Jan. 8, 2021, said application No. 17/676,711 is a continuation-in-part of application No. PCT/US2021/012694, filed on Jan. 8, 2021, application No. 17/694,366 is a continuation-in-part of application No. 16/584,737, filed on Sep. 26, 2019, now Pat. No. 11,666,780, said application No. 17/676,711 is a continuation-in-part of application No. 16/584,737, filed on Sep. 26, 2019, now Pat. No. 11,666,780, which is a continuation-in-part of application No. PCT/US2018/049400, filed on Sep. 4, 2018, application No. 17/694,366 is a continuation-in-part of application No. 16/810,204, filed on Mar. 5, 2020, now Pat. No. 11,628,310, said application No. 17/676,711 is a continuation-in-part of application No. 16/810,204, filed on Mar. 5, 2020, now Pat. No. 11,628,310, which is a continuation-in-part of application No. PCT/US2018/049400, filed on Sep. 4, 2018.

(60) Provisional application No. 62/889,461, filed on Aug. 20, 2019, provisional application No. 62/772,741, filed on Nov. 29, 2018, provisional application No. 63/126,855, filed on Dec. 17, 2020, provisional application No. 62/944,952, filed on Dec. 6, 2019, provisional application No. 62/958,554, filed on Jan. 8, 2020, provisional application No. 62/958,517, filed on Jan. 8, 2020, provisional application No. 62/958,634, filed on Jan. 8, 2020, provisional application No. 62/738,573, filed on Sep. 28, 2018.

(58) Field of Classification Search
CPC .... A61N 2005/1019; A61N 2005/1024; A61N 2005/1089; A61N 2005/1094
See application file for complete search history.

(56) References Cited

U.S. PATENT DOCUMENTS

| | | | |
|---|---|---|---|
| 5,637,073 A | 6/1997 | Freire | |
| D526,411 S | 8/2006 | Easley | |
| 7,109,505 B1 | 9/2006 | Sliski et al. | |
| 8,602,959 B1 | 12/2013 | Park et al. | |
| 8,608,632 B1 | 12/2013 | Brigatti et al. | |
| 9,056,201 B1 | 6/2015 | Hamilton et al. | |
| D748,256 S | 1/2016 | Wagner et al. | |
| D754,331 S | 4/2016 | Wargner et al. | |
| D781,420 S | 3/2017 | Korenfeld et al. | |
| D814,637 S | 4/2018 | Lohrenz et al. | |
| 10,022,558 B1 | 7/2018 | Marsteller et al. | |
| D841,164 S | 2/2019 | Flowers et al. | |
| 10,245,178 B1 | 4/2019 | Heitzmann et al. | |
| 10,576,299 B1 | 3/2020 | Munro, II et al. | |
| D939,706 S | 12/2021 | Van Manen | |
| D940,865 S | 1/2022 | Khan et al. | |
| 11,273,325 B2* | 3/2022 | Marsteller ........... | A61F 9/00781 |
| D972,138 S | 12/2022 | Holderby et al. | |
| 2003/0199883 A1 | 10/2003 | Laks | |
| 2004/0138515 A1* | 7/2004 | White .................. | A61N 5/1017 |
| | | | 600/3 |
| 2006/0111605 A1* | 5/2006 | Larsen ................. | A61N 5/1017 |
| | | | 600/1 |
| 2006/0212040 A1 | 9/2006 | Goldstein | |
| 2007/0055089 A1* | 3/2007 | Larsen ................. | A61N 5/1017 |
| | | | 600/3 |
| 2007/0118010 A1 | 5/2007 | Hillstead et al. | |
| 2011/0207987 A1 | 8/2011 | DiCarlo et al. | |
| 2012/0330088 A1 | 12/2012 | Hillstead et al. | |
| 2013/0211178 A1 | 8/2013 | Luca et al. | |
| 2015/0105601 A1 | 4/2015 | Finger et al. | |
| 2015/0105602 A1 | 4/2015 | Finger et al. | |
| 2016/0375267 A1 | 12/2016 | Lutz et al. | |
| 2017/0182063 A1 | 6/2017 | Yu et al. | |
| 2017/0216499 A1 | 8/2017 | Kaplan | |
| 2017/0258988 A1 | 9/2017 | Meyer et al. | |
| 2019/0240504 A1 | 8/2019 | Brachman et al. | |
| 2019/0259506 A1 | 8/2019 | Vose et al. | |
| 2019/0336791 A1 | 11/2019 | Shilton et al. | |
| 2020/0171323 A1 | 6/2020 | Marsteller et al. | |
| 2022/0212032 A1 | 7/2022 | Marsteller et al. | |

FOREIGN PATENT DOCUMENTS

| | | | |
|---|---|---|---|
| EP | 3031494 B1 | 8/2018 | |
| IN | 304392-0001 | 3/2019 | |
| IN | 315612-001-0001 | 2/2020 | |
| JP | 563138962 A | 6/1988 | |
| JP | 2001507969 A | 6/2001 | |
| JP | 2011508654 A | 3/2011 | |
| JP | 2016512101 A | 4/2016 | |
| JP | 2020533098 A | 11/2020 | |
| JP | D1733444 | 12/2022 | |
| WO | 2004098523 A2 | 11/2004 | |
| WO | 2005079915 A1 | 9/2005 | |
| WO | 2007106557 A2 | 9/2007 | |
| WO | 2009075714 A1 | 6/2009 | |
| WO | 2009149175 A1 | 12/2009 | |
| WO | 2010022153 A1 | 2/2010 | |
| WO | 2011053908 A1 | 5/2011 | |

(56)          References Cited

FOREIGN PATENT DOCUMENTS

| WO | 2014194959 A1 | 12/2014 | | |
| WO | WO 2017112891 | * 6/2017 | ........... | A61F 9/0008 |
| WO | WO-2017112891 A1 * | 6/2017 | ........... | A61N 5/1017 |
| WO | 2019113192 A1 | 6/2019 | | |
| WO | 2020113091 A1 | 6/2020 | | |

OTHER PUBLICATIONS

"Radiance Therapeutics: CEO Laurence Marsteller presenting at Eyecelerator 2022." Found online at youtube.com. Mar. 16, 2023. Reference dated Oct. 18, 2022. Retrieved from https://www.youtube.com/watch?v=sdkOXVcibF4.

"Physics world: Novel brachytherapy device treats eye cancer with intensity-modulated radiation." Found online at physicsworld.com. Mar. 16, 2023. Reference dated Jun. 17, 2021. Retrieved from https://physicsworld.com/a/.novel-brachytherapy-device-treats-eye-cancer-with-intensity-modulated-radiation/.

"Fastener Superstore: Standard blind rivets." Found online at amazon.com. Mar. 16, 2023. Reference dated Jan. 30, 2008. Retrieved from https://www.amazon.com/Standard-Blind-Rivets-Aluminum-Carton/dp/B005EY8550.

"Ali Express: Titanium Kuglen Iris Hook and Lens Manipulator." Found online at aliexpress.com. Mar. 16, 2023. Reference dated Nov. 30, 2022. Retrieved from https://www.aliexpress.us/item/2255800223699318.html?

Cordeiro, M. F., L. Chang, and P. T. Khaw. "The healing of ocular tissues: The basis of successful treatment of ocular disease." (2000): 101-110.

Ayyala et al., "Comparison of Different Biomaterials for Glaucoma Drainage Devices." Arch Ophthalmol v. 117 (1999):233-236, 4 pages.

Acosta et al., "A Newly Designed Glaucoma Drainage Implant Made of Poly(styrene-b-isobutylene-b-styrene)." Arch Opthalmol v. 124 (2006): 1742-1749, 8 pages.

Cabourne et al., "Mitomycin C versus 5-Fluorouracil for wound healing in glaucoma surgery." Cochrane Database of Systematic Reviews (2015), Issue 11. Art. No. CD006259, 52 pages.

Amano et al., "Comparative study of intraoperative mitomycin C and β irradiation in pterygium surgery" British Journal of Ophthalmology (2000) 84:618-621, 4 pages.

Khaw et al., "Trabeculectomy Technique." Glaucoma Today (2005) Mar./Apr. 22-29, 8 pages.

Khaw et al., 2015, ARVO Poster Abstract, 2 pages.

Erickson et al. "The American College of Radiology and the American Brachytherapy Society practice parameter for the performance of radionuclide-based high-dose-rate brachytherapy." Brachytherapy 16.1 (2017): 75-84.

* cited by examiner

Surface Dose Profile for $^{90}$Sr Source

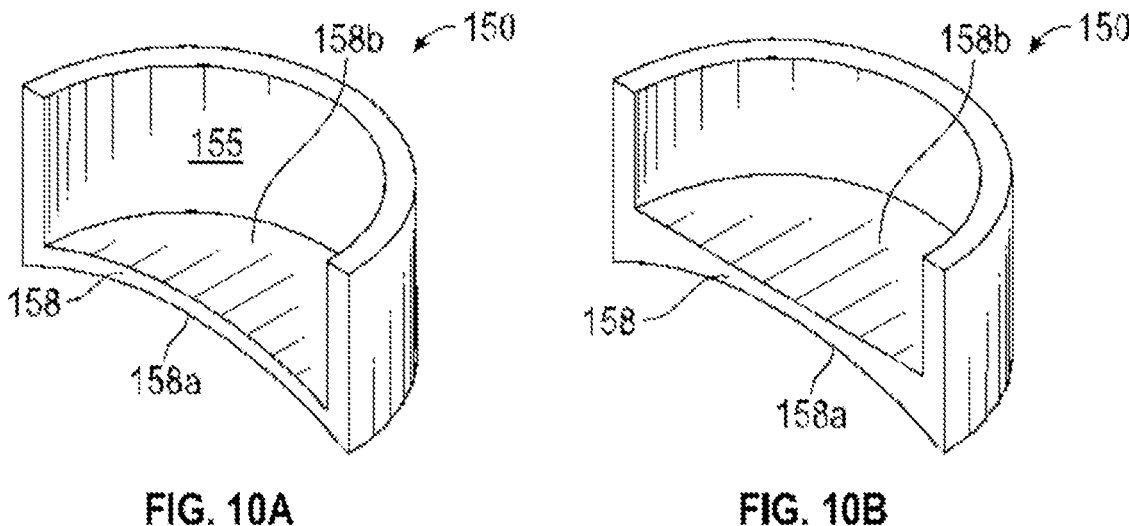
FIG. 10A          FIG. 10B
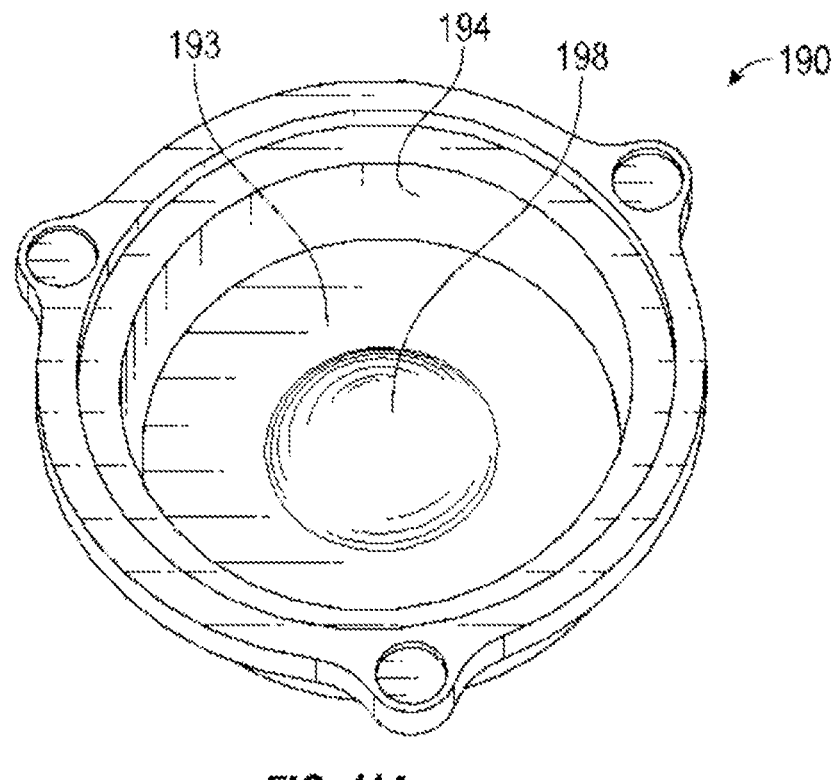
FIG. 11A

OPHTHALMIC BRACHYTHERAPY SYSTEMS AND DEVICES FOR APPLICATION OF BETA RADIATION

CROSS-REFERENCES TO RELATED APPLICATIONS

This application is a continuation-in-part of and claims priority to U.S. patent application Ser. No. 17/676,711 filed on Feb. 21, 2022, which is a continuation-in-part of and claims priority to PCT Application No. PCT/US2020/047235 filed on Aug. 20, 2020, which claims priority to U.S. Provisional Patent Application No. 62/889,461 filed on Aug. 20, 2019, the specification(s) of which is/are incorporated herein in their entirety by reference.

This application is a continuation-in-part of and claims priority to U.S. patent application Ser. No. 16/698,676 filed on Nov. 27, 2019, the specification of which is incorporated herein in their entirety by reference. U.S. Ser. No. 17/676, 711 is a continuation-in-part of and claims priority to U.S. Ser. No. 16/698,676. Ser. No. 16/698,676 claims priority to U.S. Provisional Patent Application No. 62/772,741 filed on Nov. 29, 2018, the specification of which is incorporated herein in their entirety by reference.

This application is a continuation-in-part of and claims priority to PCT Application No. PCT/US2021/064141 filed on Dec. 17, 2021, the specification of which is incorporated herein in their entirety by reference. U.S. Ser. No. 17/676, 711 is a continuation-in-part of and claims priority to PCT/US2021/064141. PCT/US2021/064141 claims priority to PCT Application No. PCT/US2021/012694 filed on Jan. 8, 2021, PCT Application No. PCT/US2021/012744 filed on Jan. 8, 2021, and U.S. Provisional Patent Application No. 63/126,855 filed on Dec. 17, 2020, the specification(s) of which is/are incorporated herein in their entirety by reference.

This application is a continuation-in-part of and claims priority to PCT Application No. PCT/US2021/064190 filed on Dec. 17, 2021, the specification of which is incorporated herein in their entirety by reference. U.S. Ser. No. 17/676, 711 is a continuation-in-part of and claims priority to PCT/US2021/064190. PCT/US2021/064190 claims priority to PCT Application No. PCT/US2021/012694 filed on Jan. 8, 2021, PCT Application No. PCT/US2021/012744 filed on Jan. 8, 2021, and U.S. Provisional Patent Application No. 63/126,855 filed on Dec. 17, 2020, the specification(s) of which is/are incorporated herein in their entirety by reference.

This application is a continuation-in-part of and claims priority to PCT Application No. PCT/US2020/063435 filed on Dec. 4, 2020, the specification of which is incorporated herein in their entirety by reference. U.S. Ser. No. 17/676, 711 is a continuation-in-part of and claims priority to PCT/US2020/063435. PCT/US2020/063435 claims priority to U.S. Provisional Patent Application No. 62/944,952 filed on Dec. 6, 2019, the specification of which is incorporated herein in their entirety by reference.

This application is a continuation-in-part of and claims priority to PCT Application No. PCT/US2021/012744 filed on Jan. 8, 2021, the specification of which is incorporated herein in their entirety by reference. U.S. Ser. No. 17/676, 711 is a continuation-in-part of and claims priority to PCT/US2021/012744. PCT/US2021/012744 claims priority to U.S. Provisional Patent Application No. 62/958,554 filed on Jan. 8, 2020, the specification of which is incorporated herein in their entirety by reference.

This application is a continuation-in-part of and claims priority to PCT Application No. PCT/US2021/012694 filed on Jan. 8, 2021, the specification of which is incorporated herein in their entirety by reference. U.S. Ser. No. 17/676, 711 is a continuation-in-part of and claims priority to PCT/US2021/012694. PCT/US2021/012694 claims priority to U.S. Provisional Patent Application No. 62/958,517 filed Jan. 8, 2020 and U.S. Provisional Patent Application No. 62/958,634 filed Jan. 8, 2020, the specification(s) of which is/are incorporated herein in their entirety by reference.

This application is a continuation-in-part of and claims priority to U.S. patent application Ser. No. 16/584,737 filed Sep. 26, 2019, the specification of which is incorporated herein in their entirety by reference. U.S. Ser. No. 17/676, 711 is a continuation-in-part of and claims priority to U.S. Ser. No. 16/584,737. U.S. Ser. No. 16/584,737 claims priority to U.S. Provisional Patent Application No. 62/738,573 filed on Sep. 28, 2018 and is also a continuation-in-part and claims priority to PCT Application No. PCT/US2018/049400 filed on Sep. 4, 2018, which claims priority to GB Application No. 1714392.6 filed Sep. 7, 2017, the specification(s) of which is/are incorporated herein in their entirety by reference.

This application is a continuation-in-part of and claims priority to U.S. patent application Ser. No. 16/810,204 filed Mar. 5, 2020, the specification of which is incorporated herein in their entirety by reference. U.S. Ser. No. 17/676, 711 is a continuation-in-part of and claims priority to U.S. Ser. No. 16/810,204. U.S. Ser. No. 16/810,204 is a continuation-in-part and claims priority to PCT Application No. PCT/US2018/049400 filed on Sep. 4, 2018, which claims priority to GB Application No. 1714392.6 filed Sep. 7, 2017, the specification(s) of which is/are incorporated herein in their entirety by reference.

BACKGROUND OF THE INVENTION

Field of the Invention

The present invention relates to systems and devices for applying radiation to a treatment area, e.g., for applying beta radiation to help maintain functioning blebs and/or drainage holes arising from glaucoma drainage procedures or surgeries, to help avoid scar formation or wound reversion, to inhibit or reduce fibrogenesis and/or inflammation in the blebs or surrounding areas, etc.

Background Art

Glaucoma

Glaucoma is the leading cause of irreversible blindness and represents a family of diseases with a characteristic optic neuropathy. Therapy for this group of diseases is principally focused at reducing the intraocular pressure (IOP) of the fluid inside the eye (aqueous humor), thus averting ongoing damage to the optic nerve.

Glaucoma is managed by attempting to lower the intraocular pressure (IOP). In the USA, Europe, and some other industrialized countries, the first line therapy is typically medication delivered by eye drops. Such medications include beta-blockers, prostaglandins, alpha-adrenergic agonists, and carbonic anhydrase inhibitors. For patients who fail medication and in other parts of the world where there are economic and distribution barriers to the practicality of daily medication and frequent follow up, the treatment regime is primarily surgical interventions.

One way to prevent vision loss from glaucoma is to lower intraocular pressure with drainage surgery that shunts fluid out of the eye through a channel created during a trabeculectomy procedure, by implanting a flow-controlled drainage device during Minimally Invasive Glaucoma Surgery (MIGS), or by the use of other surgical procedures (e.g., a Minimally Invasive Micro Sclerostomy (MIMS)) or devices. These systems and procedures allow drainage of the aqueous humor from within the eye to a small reservoir (termed a "bleb") under the conjunctiva, from where the aqueous humor is later reabsorbed.

However, scar tissue often compromises the bleb or other surrounding structures (e.g., holes associated with MIMS), ultimately impeding or blocking the flow of excess fluid. Despite compelling therapeutic advantages over nonsurgical treatments, drainage surgery and devices are clinically limited by postoperative scarring.

Attempts to address this include the application of antimetabolites such as mitomycin C (MMC) and 5-fluorouracil (5FU). These antimetabolites are used in liquid form and are delivered either by injection or by placing microsurgical sponges soaked in the drug directly onto the operative site underneath the conjunctiva. One of the problems associated with antimetabolites (e.g., MMC and 5FU) is that they do not preserve blebs well. By some reports, the failure rate by three years approaches 50%.

Beta Ophthalmic Applicators

Brachytherapy involves the placement of a radioisotope inside or next to the area requiring treatment, and has shown safety and efficacy in the clinical management of many diseases. Recently beta brachytherapy has been surprisingly found to be an efficacious therapy in the management of glaucoma drainage blebs.

Soares (Med Phys 1995, 22(9): 1487-1493) has published a paper detailing the dosimetry of typical beta ophthalmic applicators that apply a disk-shaped beta RBS to the eye. The Soares work demonstrates that, by inspection of the surface planar isodose figures, the delivered dose across the radius falls off precipitously in most of these devices. In some devices, the maximum dose is not the center point. The Soares results are similar to earlier publications such as that of Bahrassa and Datta (Int J Radiat Oncol Biol Phys 1983, 9(5): 679-84), which discloses that for a typical applicator, the dose at 3.5 mm from the center-point is only 50% of the center-point maximum dose (see FIG. 1A).

Generally, in legacy beta applicators, it seems that about 90% of the central maximum dose falls only within about the inner 2 mm diameter of the applicator disk. The dose appears to be reduced significantly further out along the diameter of the applicator disk. This relative under-dosing of the periphery is a significant portion of the total irradiated surface area and a significant portion of the volume of the irradiated target tissue. In addition, Soares also showed irregular dosage patterns and large variation between even the same model applicator. Many of the applicators did not seem to have the maximum dose active portion aligned with the center of the applicator.

Safety concerns led to the narrowing of the therapeutic area in ophthalmic applicators used for pterygium treatment by attaching field-shaping masks with the effect of providing a narrowed focal application. In 1956, Castroviejo (Trans Am Acad Ophthalmol Otolaryngol. 1956, 60(3):486) introduced a series of four screening masks designed to fit snugly over the end of the applicator. The masks are constructed of stainless steel 0.5 mm thick that substantial blocks the beta radiation and thus restricts irradiation to only that area of the cut out of the masks. These are used to reduce the active surface area of the applicator. The masks are supplied with circular areas of 3 mm or 5 mm in diameter, and elongated areas 2 mm and 3 mm wide and 8.7 mm long. However, the Castroviejo masks do not provide a uniform dose over the total area of the disk applicator. Thus, the previous art of the Castroviejo Masks is not effective for the application of irradiation of glaucoma drainage blebs.

Brachytherapy Applicator Systems and Devices of the Present Invention

The present invention features systems and devices, e.g., brachytherapy systems and devices, for applying radiation to a treatment area. For example, the systems and devices herein may be used to apply beta radiation to a target area in the eye to help maintain functioning blebs and/or drainage holes arising from glaucoma drainage procedures or surgeries, to help avoid scar formation or wound reversion, to inhibit or reduce fibrogenesis and/or inflammation in the blebs or surrounding areas, etc.

The systems and devices of the present invention feature a handle with a mechanism for attaching a radionuclide brachytherapy source therein for providing beta radiation. The systems and devices also feature radiation attenuation shields that help determine (e.g., optimize) the beta radiation dose distribution across an area of the target, e.g., a target area for treatment of glaucoma drainage bleb tissues or other treatment area. The radiation attenuation shields may also help attenuate the distribution of beta radiation to non-target tissue, such as the lens.

The present invention provides the unique technical features of the use of beta radiation instead of, or in combination with, antimetabolites in treatment of conjunctival blebs for prophylaxis and/or treatment of scar.

The present invention also provides the unique technical feature of the delivery of a more optimized dose distribution across the surface of the treatment area (target area) and/or a surface or plane within the treatment area (target area) as compared to devices previously used (see FIG. 1A).

Without wishing to limit the present invention to any theory or mechanism, as used herein, the term "optimized dose distribution" may refer to a dose across a particular plane on or within the target that is substantially uniform and therapeutic in dose. For example, the dose across the particular plane on or within the target varies by no more than a certain percentage of the maximum dose. As shown in FIG. 1B, the radiation source, e.g., radionuclide brachytherapy source (RBS), is in contact with the eye, and the radiation is emitted to a particular target plane within the target/treatment area. The target plane shown in FIG. 1B is a particular distance from the RBS and a particular distance from the top of the target area. The size and dimensions of the target and target plane may vary.

In certain embodiments, the dose across the particular target plane on or within the target varies by no more than 10% of the maximum dose. In certain embodiments, the dose across the particular plane on or within the target varies by no more than 15% of the maximum dose. In certain embodiments, the dose across the particular plane on or within the target varies by no more than 20% of the maximum dose. In certain embodiments, the dose across the particular plane on or within the target varies by no more than 30% of the maximum dose.

As previously described, doses herein may refer to the dose received by a target surface (e.g., plane surface of a particular size) at a particular depth. In certain embodiments, the particular plane on or within the target is a distance from 0 to 700 microns from the surface of the device that contacts the eye tissue. In certain embodiments, the particular plane on or within the target is a distance from 0 to 100 microns from the surface of the device that contacts the eye tissue. In certain embodiments, the particular plane on or within the target is a distance from 100 to 200 microns from the surface of the device that contacts the eye tissue. In certain embodiments, the particular plane on or within the target is a distance from 200 to 400 microns from the surface of the device that contacts the eye tissue. In certain embodiments, the particular plane on or within the target is a distance from 200 to 600 microns from the surface of the device that contacts the eye tissue. In certain embodiments, the particular plane on or within the target is a distance from 400 to 600 microns from the surface of the device that contacts the eye tissue.

In certain embodiments, the target surface (e.g., plane surface) has a diameter of about 2 mm. In certain embodiments, the target surface (e.g., plane surface) has a diameter of about 3 mm. In certain embodiments, the target surface (e.g., plane surface) has a diameter of about 4 mm. In certain embodiments, the target surface (e.g., plane surface) has a diameter of about 5 mm. In certain embodiments, the target surface (e.g., plane surface) has a diameter of about 6 mm. In certain embodiments, the target surface (e.g., plane surface) has a diameter of about 7 mm. In certain embodiments, the target surface (e.g., plane surface) has a diameter of about 8 mm. In certain embodiments, the target surface (e.g., plane surface) has a diameter of about 9 mm. In certain embodiments, the target surface (e.g., plane surface) has a diameter of about 10 mm. In certain embodiments, the target surface (e.g., plane surface) has a diameter of about 11 mm. In certain embodiments, the target surface (e.g., plane surface) has a diameter of about 12 mm. In certain embodiments, the target surface (e.g., plane surface) has a diameter from 10 to 14 mm. In certain embodiments, the target surface (e.g., plane surface) has a diameter from 6 to 10 mm. In certain embodiments, the target surface (e.g., plane surface) has a diameter from 5 to 12 mm. In certain embodiments, the target surface (e.g., plane surface) has a diameter from 6 to 12 mm. In certain embodiments, the target surface (e.g., plane surface) has a diameter from 8 to 10 mm. In certain embodiments, the target surface (e.g., plane surface) has a diameter from 6 to 8 mm. In certain embodiments, the target surface (e.g., plane surface) has a diameter from 7 to 10 mm. In certain embodiments, the target surface (e.g., plane surface) has a diameter from 8 to 11 mm. In certain embodiments, the target surface (e.g., plane surface) has a diameter from 9 to 12 mm. The present invention is not limited to the aforementioned dimensions of the target surface.

Alternatively, "optimized dose distribution" may also mean that the dose distribution is varied across the lesion in a specific pattern with the intention to best affect the therapeutic outcome. In one example, the dose distribution across the diameter/plane at the treatment depth varies such that the areas at the edges of the bleb receive a higher dose relative to the center. In one example, the dose distribution across the diameter/plane at the treatment depth varies such that the area at the MIGS device outflow orifice receives a boosted dose compared to other areas. In one example, the dose distribution across the diameter/plane at the treatment depth varies such that the edges of the bleb and also the area at the MIGS device outflow orifice both receive a boosted dose. In one example, the dose is attenuated over a specified area. In one example, the dose is attenuated over the cornea.

Beta radiation attenuates quickly with depth. In some embodiments, the term "optimized dose distribution" includes an appropriate dose through the depth of the target tissue. The clinical dosage depth may be determined by the thickness of the conjunctiva and associated tenon's capsule of a functional bleb. For MIGS surgery, the focus area may be approximately 3 mm above the superior limbus. Howlet et al., found the mean thickness of the conjunctival and Tenon's layer to be 393±67 microns ranging from 194 to 573 microns using optical coherence tomography (OCT) in glaucoma patients (Howlet J et al., Journal of Current Glaucoma Practice 2014, 8(s):63-66). In an earlier study, Zhang et al. found conjunctival thickness to be 238±51 microns in healthy individuals using OCT analysis and concluded OCT accurately measures the cross-sectional structures of conjunctival tissue with high resolution (Zhang et al., Investigative Ophthalmology & Visual Science 2011, 52(10):7787-7791). Based on the Howlet study, the target tissue thickness may range from 150 to 700 microns, or from 10 to 700 microns, etc. In one example, the dose distribution from the surface through the depth of the target tissue allows for a therapeutic dose within the tissue to the limits of the rapidly attenuating beta rays.

BRIEF SUMMARY OF THE INVENTION

The present invention features ophthalmic applicator systems and devices for applying radiation to a treatment area. While the present invention describes applications of the systems and devices for treating glaucoma drainage bleb tissues or drainage holes, the present invention is not limited to the applications disclosed herein.

The systems and devices comprise a brachytherapy applicator. The system may further comprise a radioisotope brachytherapy source (RBS). Generally, the RBS may comprise Strontium-90/Yttrium-90, sealed in a disk-shaped capsule of stainless steel or titanium, although other appropriate radioisotopes and other appropriate capsule materials can be used. The brachytherapy applicator comprises a handle and a mechanism for attaching the RBS, and may further comprise other functional features. The brachytherapy applicator enables application of the RBS to the eye so as to provide beta brachytherapy.

For example, the present invention features a brachytherapy system for applying a dose of beta radiation to a target, wherein the brachytherapy system comprises a handle having a distal end and a cap system attachable to the distal end of the handle. In some embodiments, the cap system comprises a cylindrical base ring having a first end and a second end opposite the first end and an inner cavity therein for accepting a radionuclide brachytherapy source (RBS), wherein the first end is open to allow for insertion of the RBS into the inner cavity and a barrier surface seals the second end so as to prevent passing of the RBS through the second end. In some embodiments, the cap system further comprises a shaping component disposed on an interior surface of the barrier surface in the inner cavity of the base ring, wherein the shaping component is shaped and constructed to regulate a dose of beta radiation delivered from the RBS to a target plane of a treatment area.

In some embodiments, the shaping component is dome shaped, rectangular, a round disk, or an annulus. In some embodiments, the shaping component is a combination of two or more pieces. In some embodiments, the combination of two or more pieces comprises pieces constructed from different material. In some embodiments, the shaping component is constructed from a material comprising one or a combination of: stainless steel, titanium, copper, brass, tungsten, tungsten-copper, a metal alloy, or a polymer.

In some embodiments, the cap system and the handle attach via a threaded mechanism. In some embodiments, threads are disposed on the base ring at the first end that engage threads disposed on the distal end of the handle.

In some embodiments, the system further comprises the RBS housed in the inner cavity of the base ring. In some embodiments, the RBS comprises Strontium-90 in secular equilibrium with Yttrium-90.

In some embodiments, the barrier surface is constructed from a material comprising a synthetic polymer material. In some embodiments, the base ring is constructed from a material comprising a metal, metal alloy, plastic, or a combination thereof. In some embodiments, the inner cavity of the base ring is 11 mm in diameter.

The present invention also features brachytherapy systems for applying a dose of beta radiation to a target (e.g., portion of a glaucoma drainage bleb, etc.), wherein the system comprises a cap system for accepting a radionuclide brachytherapy source (RBS) for providing the dose of beta radiation and the cap system is attachable to a handle, e.g., the cap system may be attachable (directly or indirectly) to the distal portion of the handle. The system may further comprise a radiation attenuation shield that determines (e.g., optimizes) the distribution of the dose of beta radiation to the target area. The radiation attenuation shield may be attachable to the cap system, the radiation attenuation shield may be integrated into the cap system, the radiation attenuation shield may be integrated into the handle, etc. The system may further comprise the radionuclide brachytherapy source (RBS).

The present invention also features a brachytherapy system for applying a dose of beta radiation to a target. In certain embodiments, the brachytherapy system comprises a cap system. The cap system may comprise a base ring having a first end and a second end opposite the first end and a cavity therein for accepting a radionuclide brachytherapy source (RBS) (the first end is open to allow for insertion of the RBS into the cavity); and a barrier surface sealing the second end of the base ring so as to prevent passing of the RBS through the second end. The barrier surface may be constructed from a material comprising a synthetic polymer material (e.g., plastic) and the base ring is constructed from a material comprising a metal or metal alloy.

In some embodiments, the barrier surface is attached to the second end of the base ring by vacuum forming. In certain embodiments, the base ring further comprises a ridge disposed on its outer surface, wherein the barrier surface extends over the outer surface of the base ring past the ridge. In certain embodiments, the exterior surface of the barrier surface is flat. In certain embodiments, the exterior surface of the barrier surface is concave. In certain embodiments, the exterior surface of the barrier surface is convex. In certain embodiments, the system further comprises an RBS disposed in the cavity of the base ring. In certain embodiments, the system further comprises a radiation attenuation shield attached to the cap system on the second end of the base ring, the radiation attenuation shield is constructed to regulate a dose of beta radiation delivered from an RBS to a target plane of a treatment area.

The present invention also features a brachytherapy system for applying a dose of beta radiation to a target, wherein the brachytherapy system comprises a handle having a distal end; and a cap system disposed on the distal end of the handle. The cap system comprises a base ring having a first end and a second end opposite the first end and a cavity therein for accepting a radionuclide brachytherapy source (RBS) (the first end is open to allow for insertion of the RBS into the cavity). A barrier surface seals the second end of the base ring so as to prevent passing of the RBS through the second end. In certain embodiments, the barrier surface is constructed from a material comprising a synthetic polymer material (e.g., plastic) and the base ring is constructed from a material comprising a metal or metal alloy.

With respect to any of the system embodiments herein, in certain embodiments, the barrier surface is attached to the second end of the base ring by vacuum forming. In some embodiments, the base ring further comprises a ridge disposed on its outer surface, wherein the barrier surface extends over the outer surface of the base ring past the ridge. In some embodiments, the system further comprises an RBS disposed in the cavity of the base ring. In some embodiments, the system further comprises a radiation attenuation shield attached to the cap system on the second end of the base ring, the radiation attenuation shield is constructed to regulate a dose of beta radiation delivered from an RBS to a target plane of a treatment area.

With respect to any of the system embodiments herein, in certain embodiments, the cap system is removably attached to the distal end of the handle. In some embodiments, the cap system is indirectly attached to the distal end of the handle. In certain embodiments, the system further comprises a stem extending from the distal end of the handle, wherein the cap system removably attaches to the stem of the distal end. In some embodiments, the stem is straight. In some embodiments, the stem has a curvature. In some embodiments, the stem further comprises a disc flange disposed on its end opposite the handle, wherein the cap system removably attaches to the disc flange of the stem. In some embodiments, the cap system threads onto the disc flange. In some embodiments, the cap system snaps onto the disc flange. In some embodiments, the exterior surface of the barrier surface is flat. In some embodiments, the exterior surface of the barrier surface is concave. In some embodiments, the exterior surface of the barrier surface is convex. In certain embodiments, the system further comprises an RBS disposed in the cavity of the base ring. In some embodiments, the RBS comprises Strontium-90/Yttrium-90. In some embodiments, attaching the cap system to the distal end of the handle seals an RBS in the cap system. In certain embodiments, the system further comprises a radiation attenuation shield attachable to the cap system on the second end of the base ring, the radiation attenuation shield is constructed to regulate a dose of beta radiation delivered from an RBS to a target plane of a treatment area. In some embodiments, the system delivers a substantially uniform dose of beta radiation to a target plane of a treatment area.

The present invention also features a system comprising a radiation attenuation shield that modifies the output of beta radiation from a beta radionuclide brachytherapy source (RBS) so as to provide a substantially uniform dose distribution across a treatment radius. In certain embodiments, the attenuation shield comprises a shield wall with a sealed bottom barrier forming a shield well for accepting the RBS, and a shaping component disposed on an interior surface of the bottom barrier, wherein the shaping component is shaped and constructed to regulate a dose of beta radiation delivered from the RBS to a target plane of a treatment area. In certain embodiments, the RBS is directly inserted into the shield well. In certain embodiments, the RBS is indirectly inserted into the shield well.

With respect to any of the system embodiments herein, in certain embodiments, the shaping component is dome shaped. In certain embodiments, the shaping component is a round disk. In certain embodiments, the shaping component is an annulus. In certain embodiments, the shaping component is rectangular. In certain embodiments, the shaping component is a combination of two or more pieces. In certain embodiments, the combination of two or more pieces comprises pieces constructed from different material. In certain embodiments, the combination of two or more pieces comprises pieces constructed from different sizes. In certain embodiments, the shaping component is constructed from a material comprising stainless steel. In certain embodiments, the shaping component is constructed from a material comprising one or a combination of: stainless steel, titanium, copper, brass, tungsten, tungsten-copper, a metal alloy, or a polymer. In certain embodiments, the radiation attenuation shield is constructed from a material comprising a polymer. In certain embodiments, the polymer is one or a combination of: polycarbonate, PEEK, PEI, PET, PETG, ABS, Epoxy, Polyester, Polystyrene, polyurethane, PVDF, Polyimide, HIPS, or Styrene-butadiene rubber.

With respect to any of the system embodiments herein, in certain embodiments, the shaping component has a thickness from 0.01 mm to 1.5 mm. In certain embodiments, the shaping component has a thickness of 0.05 mm. In certain embodiments, the shaping component has a thickness from 0.01 mm to 1 mm. In certain embodiments, the shaping component has a thickness from 0.1 mm to 0.5 mm. In certain embodiments, the shaping component has a diameter from 1 mm to 5 mm. In certain embodiments, the shaping component has a diameter of 3 mm. In certain embodiments, the shaping component has a diameter from 2 mm to 5 mm. In certain embodiments, the shaping component is a stainless steel disc with a diameter of 3 mm and a thickness of 0.05 mm. In certain embodiments, the shaping component is a stainless steel annulus with an outer diameter of 3.5 mm, an inner diameter of 2 mm, and a thickness of 0.05 mm. In certain embodiments, the shaping component attenuates beta radiation by 5-90%, e.g., 50%. In certain embodiments, the shaping component is stainless steel foil. In certain embodiments, the shaping component is in a shape of a disc or annulus. In certain embodiments, the shaping component is kidney shaped.

With respect to any of the embodiments herein, in certain embodiments, the target plane of the treatment area has a diameter is from 8 to 12 mm. In certain embodiments, the target plane of the treatment area has a diameter is from 9 to 11 mm. In certain embodiments, the dose at any point on the target plane of the treatment area is within 10% of a dose at any other point on the target plane of the treatment area. In certain embodiments, the dose at any point on the target plane of the treatment area is within 20% of a dose at any other point on the target plane of the treatment area. In certain embodiments, the dose at any point on the target plane of the treatment area is within 30% of a dose at any other point on the target plane of the treatment area. In certain embodiments, the target plane of the treatment area is 0 to 700 microns from a surface of the system that contacts eye tissue over the treatment area of the eye. In certain embodiments, the target plane is from 8 to 12 mm in diameter.

With respect to any of the embodiments herein, in certain embodiments, the attenuation shield comprises a shield wall with a sealed bottom barrier forming a shield well for accepting the second end of the base ring of the cap system, and a shaping component disposed on an interior surface of the bottom barrier, wherein the shaping component is shaped and constructed to regulate a dose of beta radiation delivered from an RBS to a target plane of a treatment area. In certain embodiments, the attenuation shield snaps onto the cap system. In certain embodiments, the attenuation shield is fixedly attached to the cap system. For example, in certain embodiments, the attenuation shield is welded to the cap system. In certain embodiments, the attenuation shield is adhered to the cap system.

In certain embodiments, the system is for single use. In certain embodiments, the cap system is shaped to minimize movement of the RBS once the RBS is inserted therein. In certain embodiments, the system can be sterilized.

In certain embodiments, the system is for treating glaucoma treatment-associated blebs. In certain embodiments, the system is for preventing scar formation associated with implantation of a foreign body in an eye. In certain embodiments, the system is for maintaining a functioning drainage bleb in an eye. In certain embodiments, the system is for preventing wound reversion in an eye. In certain embodiments, the system is for inhibiting fibrogenesis or inflammation associated with a bleb.

In some embodiments, the system herein is constructed from a material comprising stainless steel, titanium, gold, a ceramic, a polymer, or a combination thereof.

In certain embodiments, the system herein is used in combination with application of a drug. In some embodiments, the drug is an anti-metabolite.

The present invention also features brachytherapy systems according to the present invention for use in a method of treating glaucoma. The method may comprise implanting a Minimally Invasive Glaucoma Surgery (MIGS) implant within the eye of a patient being treated for glaucoma, wherein the implant is implanted trans-sclerally to form a bleb in the subconjunctival space or between the conjunctiva and Tenon's capsule; however, the present invention is not limited to MIGS and may include MIMS or other appropriate surgical techniques and procedures. The method comprises applying beta radiation from a radioisotope in the brachytherapy system to a target area of the eye, wherein the target area is at least a portion of the bleb. In some embodiments, the method is effective to maintain a functioning drainage bleb.

The present invention also features brachytherapy systems according to the present invention for use in preventing or reducing scar formation in a draining bleb in a human eye being treated or having been treated for glaucoma (e.g., with a minimally invasive glaucoma surgery (MIGS) implant, with MIMS, etc.), characterized in that a radioisotope is administered to the eye such that beta radiation from the radioisotope is applied to a target area of the eye, the target area is at least a portion of the bleb.

The present invention also features brachytherapy systems according to the present invention for use in a method of treating glaucoma in an eye wherein a Minimally Invasive Glaucoma Surgery (MIGS) implant is implanted trans-sclerally to form a bleb in the subconjunctival space or between the conjunctiva and Tenon's capsule, characterized in that the system is applied to the eye such that beta radiation from a source of beta radiation is applied to a target area of the eye, wherein the target area is at least a portion of the bleb.

The present invention also features a method of maintaining a functioning drainage bleb in the eye of a patient being treated for glaucoma. In some embodiments, the method comprises implanting a Minimally Invasive Glaucoma Surgery (MIGS) implant within the eye, wherein the implant is inserted trans-sclerally and causes formation of a bleb in the subconjunctival space of the eye or in a space between the conjunctiva and Tenon's capsule, the bleb functions to drain aqueous humor; however, the present invention is not limited to MIGS and may include MIMS or other appropriate surgical procedures. The method further comprises applying using a brachytherapy system according to the present invention a radioisotope that emits beta radiation to a target area of the eye, wherein the target area is at least a portion of the bleb; wherein the beta radiation reduces or inhibits a fibrotic process and inflammation that causes bleb failure, and wherein the method is effective to maintain the drainage function of the bleb.

The present invention also features a method of inhibiting or reducing fibrogenesis and inflammation in a bleb of an eye being treated for glaucoma, wherein a Minimally Invasive Glaucoma Surgery (MIGS) implant is inserted trans-sclerally and causes formation of a bleb in the subconjunctival space of the eye or in a space between the conjunctiva and Tenon's capsule. In some embodiments, the method comprises applying using a brachytherapy system according to the present invention a radioisotope that emits beta radiation to a target area of the eye, wherein the target area is at least a portion of the bleb; wherein the beta radiation causes cell cycle arrest in fibroblasts on the Tenon's capsule to inhibit or reduce the fibrotic process and inflammation that leads to bleb failure.

The present invention also features a method of treating glaucoma. In some embodiments, the method comprises implanting a Minimally Invasive Glaucoma Surgery (MIGS) implant within an eye of a patient being treated for glaucoma, wherein the implant is inserted between an anterior chamber of the eye and a subconjunctival space of the eye or between the anterior chamber of the eye and a space between the conjunctiva and Tenon's capsule, the implant causes formation of a bleb for draining aqueous humor; however, the present invention is not limited to MIGS and may include MIMS or other appropriate surgical procedures. The method further comprises applying using a brachytherapy system according to the present invention a radioisotope that emits beta radiation to a target area of the eye, wherein the target area is at least a portion of the bleb; wherein the method is effective for reducing an Intraocular Pressure (IOP) of the eye.

The present invention also features a method of reducing intraocular pressure (IOP) in an eye. In some embodiments, the method comprises implanting a Minimally Invasive Glaucoma Surgery (MIGS) implant within an eye of a patient being treated for glaucoma, wherein the implant is inserted between an anterior chamber of the eye and a subconjunctival space of the eye or between the anterior chamber of the eye and a space between the conjunctiva and Tenon's capsule, the implant causes formation of a bleb for draining aqueous humor; however, the present invention is not limited to MIGS and may include MIMS or other appropriate surgical procedures. The method further comprises applying using a brachytherapy system according to the present invention a radioisotope that emits beta radiation to a target area of the eye, wherein the target area is at least a portion of the bleb; wherein the beta radiation is effective for reducing an Intraocular Pressure (IOP) of the eye.

The present invention also features a method of reducing inflammation in an eye having a foreign body therein, the foreign body being a Minimally Invasive Glaucoma Surgery (MIGS) implant inserted between an anterior chamber of the eye and a subconjunctival space of the eye or between the anterior chamber of the eye and a space between the conjunctiva and Tenon's capsule, the implant causes formation of a bleb for draining aqueous humor. In some embodiments, the method comprises applying using a brachytherapy system according to the present invention a radioisotope that emits beta radiation to a target area of the eye, wherein the target area is at least a portion of the bleb; wherein the method is effective for reducing inflammation caused by the presence of the foreign body.

The present invention also features a method of modifying a wound healing process in an eye. In some embodiments, the method comprises applying to a target of the eye beta radiation using a brachytherapy system according to the present invention. In some embodiments, the target area is a wound. In some embodiments, the target area is scar tissue. In some embodiments, the method is effective to modify cellular signaling processes that regulate wound healing so as to reduce inflammation and reduce accumulation of scar tissue. In some embodiments, the method is effective for preventing the further accumulation of scar tissue.

The present invention also features a method of breaking up scar tissue in an eye of a patient. In some embodiments, the method comprises applying to a target of the eye beta radiation using a brachytherapy system according to the present invention. In some embodiments, the scar tissue is a result of a presence of a foreign body. In some embodiments, the scar tissue is a result of a trabeculectomy. In some embodiments, the scar tissue is a result of an ocular injury. In some embodiments, the method comprises needling scar tissue. In some embodiments, the method is effective to prevent the further accumulation of scar tissue. In some embodiments, the target is a bleb or a portion thereof, a hole, or a foreign body.

For any of the system embodiments herein, in certain embodiments, the shaping component (198) attenuates from 5-50% of the beta radiation by 5-50%. In certain embodiments, the shaping component (198) attenuates from 5-50% of the beta radiation by 25-75%. In certain embodiments, the shaping component (198) attenuates from 5-50% of the beta radiation by 10-20%. In certain embodiments, the shaping component (198) attenuates from 5-50% of the beta radiation by 25-50%. In certain embodiments, the shaping component (198) attenuates from 25-75% of the beta radiation by 5-50%. In certain embodiments, the shaping component (198) attenuates from 25-75% of the beta radiation by 25-75%. In certain embodiments, the shaping component (198) attenuates from 25-75% of the beta radiation by 10-20%. In certain embodiments, the shaping component (198) attenuates from 25-75% of the beta radiation by 25-50%.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

Terms

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. The term "comprising" means that other elements can also be present in addition to the defined elements presented. The use of "comprising" indicates inclusion rather than limitation. Stated another way, the term "comprising" means "including principally, but not necessary solely". Furthermore, variation of the word "comprising", such as "comprise" and "comprises", have correspondingly the same meanings. In one respect, the technology described herein related to the herein described compositions, methods, and respective component(s) thereof, as essential to the invention, yet open to the inclusion of unspecified elements, essential or not ("comprising").

All embodiments disclosed herein can be combined with other embodiments unless the context clearly dictates otherwise.

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references Dosimetry techniques include film dosimetry. In one example the RBS is applied to radiographic film, for example Gafchromic™ film. The dose at various depths can also be measured by placing an intervening material, such as Plastic Water™, of known thicknesses between the RBS and the film. A transmission densitometer in conjunction with a film optical density vs. dose chart, allows for the film opacity to be measured and then converted to delivered dose. Other methods include Thermoluminescent methods (TLD chips). TLD chips are small plastic chips with millimeter dimensions having a crystal lattice that absorbs ionizing radiation.

Dose variation is described as that across the diameter assuming a central point maximum dose. However, in practice it has been demonstrated that the maximum dose may be off center. Thus, a description of variation of dose across the diameter may also include the variation of dose over the area, and though the depth.

In general use in the profession of ophthalmology the term "conjunctivae" may refer to the conjunctivae in combination with the Tenon's capsule. Also, in general use in the profession of ophthalmology the term "conjunctivae" may refer to the conjunctivae alone, not including the Tenon's capsule. References herein to "conjunctivae" can include either and/or both meanings.

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

Beam Modification: Desirable modification in the spatial distribution of radiation (e.g., within the patient) by insertion of any material in the beam path. Beam modification increases conformity allowing a higher dose delivery to the target, while sparing more of normal tissue simultaneously. There are four main types of beam modification: (1) Shielding: To eliminate radiation dose to some special parts of the zone at which the beam is directed. In general use is the fabrication of low-melting-temperature alloy (Lipowitz metal or Cerroblend) shielding blocks that are custom made for the individual patient and used to shield normal tissue and critical organs. For example, during total body irradiation (TBI), customized shielding blocks are positioned in front of the lungs to reduce radiation dose. (2) Compensation: To allow normal dose distribution data to be applied to the treated zone, when the beam enters obliquely through the body, or where different types of tissues are present. (3) Wedge filtration: Where a special tilt in isodose curves is obtained. (4) Flattening: Where the spatial distribution of the natural beam is altered by reducing the central exposure rate relative to the peripheral. In general use is a beam flattening filter that reduces the central exposure rate relative to that near the edge of the beam. This technique is used for linear accelerators. The filter is designed so that the thickest part is in the center. These are often constructed of copper or brass.

Innovations such as stereotaxic radiotherapy, intensity modulated radiation therapy, and conformal radiotherapy are also applied towards the goal of sparing normal tissue and critical organs. For example, Linear Accelerators designed with Multileaf Collimators have, in many circumstances, replaced shielding bocks.

Brachytherapy (see also Radionuclide Brachytherapy Source (RBS): According to the American Association of Physicists in Medicine (AAPM), brachytherapy is "the clinical use of small encapsulated radioactive sources at a short distance from the target volume for irradiation of malignant tumors or nonmalignant lesions." Generally, in medical practice, brachytherapy can be categorized as topical or plaque brachytherapy, intracavitary, and interstitial.

Some implementations of brachytherapy employ permanently implanted Radionuclide Brachytherapy Sources (RBSs). For example, in Low Dose Rate (LDR) brachytherapy for prostate cancer, a standard of care treatment, radioactive Iodine-125 RBSs are placed directly into the prostate where they remain indefinitely. In another implementation, High Dose Rate (HDR) brachytherapy TheraSpheres are infused into the arteries that feed liver tumors. These microspheres then embolize, lodging themselves in the liver's capillaries and bathing the malignancy in high levels of yttrium-90 radiation. In both these implementations, the total dose is given by consuming the entire radioisotope. Some other implementations of brachytherapy employ a transient placement of the RBS. For example, in after-loaded High Dose Rate (HDR) brachytherapy, very tiny plastic catheters are placed into the prostate gland, and a series of radiation treatments is given through these catheters. A computer-controlled machine pushes a single highly radioactive iridium-192 RBS into the catheters one by one for a specified dwell time at locations throughout the volume being irradiated. The catheters are then easily pulled out, and no radioactive material is left at the prostate gland. Another example of transient placement of an RBS includes prophylactic therapy for restenosis of coronary arteries after stent implantation. This is a non-malignant condition that has been successfully treated by placing a catheter into the coronary artery, then inserting an HDR radioactive source into the catheter and holding it there for a predetermined time in order to deliver a sufficient dose to the vessel wall.

Drainage Device or Drainage System: Any or a combination of the general and specific approaches for draining aqueous humor, such as the therapeutic and devices described herein, e.g., minimally invasive glaucoma surgery (MIGS) devices and surgery, Minimally Invasive Micro Sclerostomy (MIMS) devices and surgery, trabeculectomy surgery, sclerostomy, etc., that are employed to reduce intraocular pressure (IOP) by means of surgical intervention with or without a device.

Flow Controlled Stents (see also Minimally Invasive Glaucoma Surgery (MIGS)): Some MIGS-associated devices control flow of the aqueous humor. For example, the XEN® gel stent (Allergan) is a gelatin and glutaraldehyde tube, which is preloaded in a disposable injector and implanted using an ab interno approach. The surgeon inserts the injector through a clear cornea incision and tunnels through the sclera at or anterior to Schlemm's canal to deploy the distal portion of the stent within the subconjunctival space. This creates a pathway for aqueous to flow from the anterior chamber to the subconjunctival space, forming a bleb. Another flow-controlled stent is the InnFocus MicroShunt® (InnFocus, Santen). The surgeon inserts this device into the anterior chamber through an ab externo approach, creating a bleb in the subconjunctival space.

Functioning Drainage Bleb: A bleb that is effective for draining aqueous humor from the eye to reduce intraocular pressure (IOP) of the eye to an appropriate level.

Early bleb grading systems included those proposed by Kronfeld (1969), Migdal and Hitchings (1983), and Picht and Grehn (1998). Subsequent bleb grading systems identified and incorporated a graded assessment of various bleb parameters such as vascularity, height, width, microcystic changes, encystment and diffuse/demarcated zones.

There are two recently described grading systems for clinical grading of filtering surgery blebs: the Moorfields Bleb Grading System (MBGS) and the Indiana Bleb Appearance Grading Scale (IBAGS). The MBGS built upon the system used for this tele-medicine study and expanded it to include an assessment of vascularity away from the center of the bleb and a way to represent mixed-morphology blebs. In this scheme, central area (1-5), maximal area (1-5), bleb height (1-4) and subconjunctival blood (0-1) were assessed. In addition, three areas of the bleb were graded separately for vascularity, including bleb center conjunctiva, peripheral conjunctiva and non-bleb conjunctiva. Vascularity in each area was assigned a score from 1 to 5. A study found good inter-observer agreement and clinical reproducibility in the IBAGS and MBGS (Wells A P, Ashraff N N, Hall R C, et al. Comparison of two clinical bleb grading systems. Ophthalmology 2006; 113:77-83.)

The Moorfields bleb grading system was developed as the importance of bleb appearance to outcome was realized. Blebs that develop thin avascular zones are at increased risk of leakage and late hypotony as well as sight threatening bleb related infections.

The Indiana Bleb Appearance Grading Scale is a system for classifying the morphologic slit lamp appearance of filtration blebs. The Indiana Bleb Appearance Grading Scale contains a set of photographic standards illustrating a range of filtering bleb morphology selected from the slide library of the Glaucoma Service at the Indiana University Department of Ophthalmology. These standards consist of slit lamp images for grading bleb height, extent, vascularity, and leakage with the Seidel test. For grading, the morphologic appearance of the filtration bleb is assessed relative to the standard images for the 4 parameters and scored accordingly.

For reference, a failed or failing bleb may have "restricted posterior flow with the so-called 'ring of steel'," e.g., a ring of scar tissue or fibrosis adhering the conjunctiva to the sclera at the periphery of the bleb that restricts the flow of aqueous humor (see Dhingra S, Khaw P T. The Moorfields Safer Surgery System. Middle East African Journal of Ophthalmology. 2009; 16(3):112-115). Other attributes of failed or failing blebs may include cystic appearance and/or changes in vascularization and/or scar tissue and/or thinning of the conjunctiva overlaying the bleb and/or a tense bleb and/or other observable or measurable changes as may be included in either the Indiana Bleb Appearance Grading Scale or Moorfields Bleb Grading System. Other functional determinates of failed or failing blebs or glaucoma surgery may include increased IOP, or IOP that has not decreased sufficiently.

Minimally Invasive Glaucoma Surgery (MIGS): MIGS is a recent innovation in the surgical treatment of glaucoma developed to minimize the complications from tubes and trabeculectomy. MIGS is a term applied to the widening range of implants, devices, and techniques that seek to lower intraocular pressure with less surgical risk than the more established procedures. In most cases, conjunctiva-involving devices require a subconjunctival bleb to receive the fluid and allow for its extraocular resorption. Flow-controlled conjunctiva-involving devices typically attempt to control flow and lower IOP to normal pressure and also minimizing hypotony (too low pressure in the eye) by applying Poiseuille's law of laminar flow to create a tube that is sufficiently long and narrow to restrict and control outflow. Some MIGS devices include Flow Controlled Stents, microshunts to Shlemm's Canal, Suprachoroidal Devices, and devices for Trabeculotomy. Examples of microshunts to Schlemm's Canal include iStent® (Glaukos®) and Hydrus™ (Ivantis). Examples of suprachoroidal devices include CyPass® (Alcon), Solx® gold shunt (Solx), and iStent Supra® (Glaukos). An example of a trabeculotomy device includes the Trabectome® (NeoMedix) electrocautery device.

Planning Treatment Volume or Planning Target Volume (PTV): An area or volume that encloses all the tissue intended for irradiation. The PTV includes the clinical target volume or clinical treatment volume (CTV).

Radioactive isotope, radionuclide, radioisotope: An element that has an unstable nucleus and emits radiation during its decay to a stable form. There may be several steps in the decay from a radioactive to a stable nucleus. There are four types of radioactive decay: alpha, beta negative, beta positive, and electron capture. Gamma rays can be emitted by the daughter nucleus in a de-excitation following the decay process. These emissions are considered ionizing radiation because they are powerful enough to liberate an electron from another atom.

Therapeutic radionuclides can occur naturally or can be artificially produced, for example by nuclear reactors or particle accelerators. Radionuclide generators are used to separate daughter isotopes from parent isotopes following natural decay.

Non-limiting examples of radioactive isotopes following one of the four decay processes are given herein: (1) Alpha decay: radium 226, americium 241; (2) Beta minus: iridium 192, cesium 137, phosphorous 32 (P-32), strontium 90 (Sr-90), yttrium 90 (Y-90), ruthenium 106, rhodium-106; (3) Beta positive: fluorine 18; (4) Electron capture: iodine 125, palladium 106. Examples of gamma emission include iridium 192 and cesium 137.

Half-life is defined as the time it takes for one-half of the atoms of a radioactive material to disintegrate. Half-lives for various radioisotopes can range from a few microseconds to billions of years.

The term activity in the radioactive-decay processes refers to the number of disintegrations per second. The units of measure for activity in a given source are the curie (Ci) and becquerel (Bq). One (1) Becquerel (Bq) is one disintegration per second.

An older unit is the Curie (Ci), wherein one (1) Ci is $3.7 \times 10^{10}$ Bq.

Radionuclide Brachytherapy Source (RBS) (see also Brachytherapy): According to the US Federal Code of Regulations, a Radionuclide Brachytherapy Source (RBS) is "a device that consists of a radionuclide what may be enclosed in a sealed container made of gold, titanium, stainless steel, or platinum and intended for medical purposes to be placed onto a body surface or into a body cavity or tissue as a source of nuclear radiation for therapy." Other forms of brachytherapy sources are also used in practice. For example, a commercially available conformal source is a flexible, thin film made of a polymer chemically bound to Phosphorous-32 (P-32). Another product is the TheraSphere, a radiotherapy treatment for hepatocellular carcinoma (HCC) that consists of millions of microscopic, radioactive glass microspheres (20-30 micrometers in diameter) containing Yttrium-90. Other forms of brachytherapy employ x-ray generators as sources instead of radioisotopes.

Sclerostomy: A procedure in which the surgeon makes a small opening in the sclera to reduce intraocular pressure (IOP), usually in patients with open-angle glaucoma. It is classified as a type of glaucoma filtering surgery. Minimally invasive micro sclerostomy (MIMS, Sanoculis) is a recent innovative technique that combines the mechanism of conventional trabeculectomy and simple needling. In the course of the surgery, a sclero-corneal drainage channel is created. The MIMS procedure can be performed ab externo by creating a sclero-corneal channel to drain the aqueous humor from the anterior chamber to the subconjunctival space. The channel created with MIMS is designed to obtain a controlled fluid flow. Laser sclerostomy can be performed in a less invasive manner than standard filtering surgery. Other studies have explored the use of laser energy of varying wavelengths, properties, and tissue interaction to create thermal sclerostomies. Several methods deliver laser energy by mirrored contact lenses to the internal face of the filtration angle or by fiberoptic cables for ab interno or ab externo sclerostomy formation.

Trabeculectomy: A procedure wherein a small hole is made in the sclera and is covered by a thin trap-door. Aqueous humor drains through the trap door to a bleb. As an example, in some trabeculectomy procedures, an initial pocket is created under the conjunctiva and Tenon's capsule and the wound bed is treated with mitomycin C soaked sponges using a "fornix-based" conjunctival incision at the corneoscleral junction. A partial thickness scleral flap with its base at the corneoscleral junction after cauterization of the flap area is created. Further, a window opening is created under the flap with a Kelly-punch or a Khaw Descemet Membrane Punch to remove a portion of the sclera, Schlemm's canal, and the trabecular meshwork to enter the anterior chamber. An iridectomy is done in many cases to prevent future blockage of the sclerostomy. The scleral flap is then sutured loosely back in place with several sutures. The conjunctiva is closed in a watertight fashion at the end of the procedure.

Trans-scleral Drainage Devices: Devices that shunt aqueous humor from the anterior chamber to a subconjunctival reservoir. As an example, the EX-PRESS® Glaucoma Filtration Device channels aqueous humor through a secure lumen to a half-thickness scleral flap, creating a subconjunctival filtration bleb. The device's lumen provides a standardized opening for aqueous humor flow while also providing some resistance, which appears to add further stability to the anterior chamber during surgery and the early post-op period.

Treat, Treatment, Treating: These terms refer to both therapeutic treatments, e.g., elimination of a disease, disorder, or condition, and prophylactic or preventative measures, e.g., preventing or slowing the development of a disease or condition, reducing at least one adverse effect or symptom of a disease, condition, or disorder, etc. Treatment may be "effective" if one or more symptoms or clinical markers are reduced as that term is defined herein. Alternatively, a treatment may be "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom (s), diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with a particular disease, disorder, or condition, as well as those likely to develop a particular disease, disorder, or condition due to genetic susceptibility or other factors.

Valves: Devices that can be used for glaucoma treatment, wherein instead of using a natural bleb, these devices use a synthetic reservoir (or plate), which is implanted under the conjunctiva to allow flow of aqueous fluid. Valve devices include the Baerveldt® implant (Pharmacia Co.), the Ahmed® glaucoma valve (New World Medical), the Krupin-Denver eye valve to disc implant (E. Benson Hood Laboratories), and the Molteno® and Molteno3® drainage devices (Molteno® Ophthalmic Ltd.).

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 10A shows a cross-sectional view of a cap system of a brachytherapy applicator of the present invention.

FIG. 10B shows a cross-sectional view of a cap system of a brachytherapy applicator of the present invention.

FIG. 11A shows a perspective view of a radiation attenuation shield.

DETAILED DESCRIPTION OF THE INVENTION

Figure 1A:
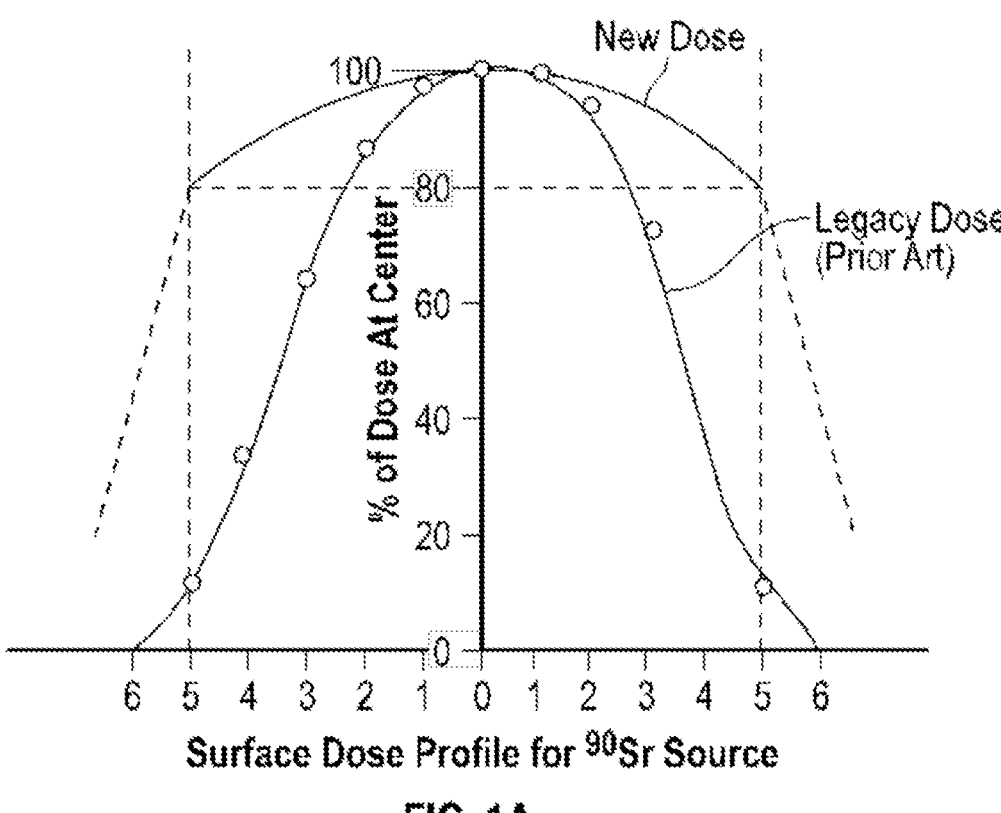
FIG. 1A shows surface dose profiles for a Sr-90 Source (from Bahrassa, 1983) (legacy dose) and a Sr-90 source of the present invention (new dose).

The present invention features ophthalmic applicator systems and devices for applying radiation to a treatment area. The systems and devices may comprise a brachytherapy applicator and may further comprise a radioisotope brachytherapy source (RBS). The systems and devices may comprise a cap system for accepting an RBS and may further comprise the RBS and/or a handle. The systems and devices of the present invention provide for a method of treating blebs or other appropriate structures or tissues, e.g., structures or tissues associated with glaucoma drainage surgery, e.g., glaucoma procedure conjunctival blebs, with a substantially uniform dose of beta therapy. While the present invention describes applications of the systems and devices for treating glaucoma drainage bleb tissues or drainage holes, the present invention is not limited to the applications disclosed herein. For example, the systems and devices may feature applying beta radiation to ocular wounds, such as wounds due to the presence of a foreign body or trauma.

Isotopes and Radioactivity

The US Nuclear Regulatory Commission (USNRC) defines radioactivity as "the amount of ionizing radiation released by a material. Whether it emits alpha or beta particles, gamma rays, x-rays, or neutrons, a quantity of radioactive material is expressed in terms of its radioactivity (or simply its activity), which represents how many atoms in the material decay in a given time period. The units of measure for radioactivity are the curie (Ci) and becquerel (Bq)." Activity in a radioactive-decay process is defined as the number of disintegrations per second, or the number of unstable atomic nuclei that decay per second in a given sample. Activity is expressed in the International System of Units by the becquerel (abbreviated Bq), which is exactly equal to one disintegration per second. Another unit that may be used is the Curie, wherein one curie is approximately the activity of 1 gram of radium and equals (exactly) $3.7 \times 10^{10}$ becquerel. The specific activity of radionuclides is relevant when it comes to select them for production for therapeutic pharmaceuticals.

By the USNRC definition, absorbed dose is defined as the amount of radiation absorbed, e.g., the amount of energy that radioactive sources deposit in materials through which they pass or the concentration of energy deposited in tissue as a result of an exposure to ionizing radiation. The absorbed dose is equal to the radiation exposure (ions or Ci/kg) of the radiation beam multiplied by the ionization energy of the medium to be ionized. Typically, the units for absorbed dose are the radiation absorbed dose (rad) and gray (Gy). Gy is a unit of ionizing radiation dose defined as the absorption of one joule of radiation energy per kilogram of matter. The rad has generally been replaced by the Gy in SI derived units. 1 Gy is equivalent to 100 rad.

Radionuclide generators are devices that produce a useful short-lived medical radionuclide (known as "daughter" products) from the radioactive transformation of a long-lived radionuclide (called a "parent"). By having a supply of parent on hand at a facility, the daughter is continually generated on site. The generator permits ready separation of the daughter radionuclide from the parent. One of the most widely used generator devices (often referred as a "cow") is the technetium 99 generator. It allows the extraction of the metastable isotope 99mTc of technetium from a source of decaying molybdenum-99. 99Mo has a half-life of 66 hours and can be easily transported over long distances to hospitals where its decay product technetium-99m (with a half-life of only 6 hours, inconvenient for transport) is extracted and used for a variety of nuclear medicine procedures, where its short half-life is very useful.

Generators can also be constructed for supply of other daughter radioisotopes. Ruthenium 106 (Ru-106) is a commercially available radioisotope with a half-life of 668373 days, making it a good candidate for a parent isotope in a cow or generator. The decay of Ru-106 to rhodium-106 (Rh-106) produces only a low energy beta of 39 Key that is not useful for therapy. However, Rh-106 has an energetic beta decay useful for brachytherapy: Rh-106 has a half-life of 30 seconds and decays by beta emission to palladium 106 (Pd-106) with a maximum decay energy of 3.541 Mev and an average energy of 96.9 Key. As an example, in some embodiments, the present invention features a device loaded from a Ruthenium-106 cow with an activity of rhodium-106 providing for the full prescribed dose. The device can be applied to the target volume to deliver the full activity of its contents. For example, the device may be placed over the target lesion for 10 half-lives (300 seconds), delivering all its radioactive energy and consuming the rhodium-106, depleting it to palladium.

In some embodiments, the present invention features the use of Ru-106 in secular equilibrium with Rh-106. Ru-106 decays by beta radiation to Rh-106. The two isotopes are in secular equilibrium with the decay rate of the combined source controlled by the Ru-106 parent but with the therapeutic beta radiations emanating from the daughter Rh-106.

Yttrium-90 is commercially available from Strontium-90 cows. As another example, in some embodiments, the present invention features the use of Yttrium-90 with a half-life of 64 hours. Y-90 decays to Zirconium 90 (Zr-90), a stable isotope, along three different routes via beta emission, wherein 99.985% of the time it decays with a maximum beta particle energy of 2.2801 MeV and a mean beta particle energy of 0.9337 MeV, or approximately or 1.5×10-13 joules. The other minor decay paths produce additional low energy gamma-rays, and electrons. Compared to the dominant path, the radiation doses from these paths are clinically negligible.

Currently, strontium-90 is also commercially available. As another example, in some embodiments, the present invention features the use of Strontium 90 (Sr-90) in secular equilibrium with Yttrium 90 (Y-90). Strontium 90 (Sr-90) decays by beta radiation to Yttrium 90 (Y-90). The parent Sr-90 isotope has a half-life of 28.79 years. The daughter Y-90 isotope has a half-life of 64.0 hours. The two isotopes are in secular equilibrium with the decay rate of the combined source controlled by the Sr-90 parent but with the therapeutic beta radiations emanating from the daughter Y-90 with maximum energy of 2.28 MeV and an average energy of 934 keV.

The Planning Target Volume (PTV) or Planning Treatment Volume (PTV) is a geometrical concept introduced for radiation treatment planning. The PTV has historically been used to ensure that the prescribed dose is actually delivered to all parts of the target tissue. Without limiting the invention to any particular surgical practice, a medical journal article details the surgical creation of the bleb in which "the surgeon dissects backward with Westcott scissors to make a pocket approximately 10 to 15 mm posteriorly and sufficiently wide to accommodate the antimetabolite sponges." In this example, the surgeon opened the potential space under the conjunctiva and Tenon's capsule creating an approximately 10 to 15 mm diameter bleb site. As an example, in this embodiment, the PTV could be defined as a disk of diameter 15 mm and depth of 0.3 mm, containing the conjunctiva and Tenon's capsule tissue.

As an example, a prescription dose of brachytherapy of 10 Gray (1000 cGy) is 10 joules/kg absorbed dose throughout the Target Volume. Measurements have suggested a model Sr-90/Y-90 RBS with Activity of 1.48 GBq produces a surface dose rate of approximately 0.20 Gy per second. To deliver a dose of 10 Gy to the Target Volume would require an irradiation time of 50 seconds. The number nuclei that decay during this 50 second treatment would be $1.48 \times 10^9$ Bq (disintegrations per second)×50 seconds=$7.4 \times 10^{10}$.

Biological Effects of Radiation

The biological effectiveness of radiation depends on the linear energy transfer (LET), total dose, fractionation rate, and radiosensitivity of the targeted cells or tissues. As radiation interacts with matter, it loses its energy through interactions with atoms in its direct path. In radiation therapy, LET is defined as the average amount of energy lost per defined distance in tissue, as in the energy deposited into a handful of cells. LET occurs at different rates in different tissues, and quantification of LET in cellular systems is an important component of determining correct dosage in radiology. Low LET radiations are X-rays, gamma rays and beta particles.

Radiation induced ionizations can act directly on the cellular molecules and cause damage, such as DNA damage. Radiation induced ionizations also can act indirectly, producing free radicals that are derived from the ionization or excitation of the water component of the cell. Exposure of cells to ionizing radiation induces high-energy radiolysis of $H_2O$ water molecules into H+ and OH– radicals. These radicals are themselves chemically reactive, and in turn recombine to produce a series of highly reactive combinations such as superoxide ($O_2^-$) and peroxide ($H_2O_2$) that produce oxidative damage to molecules, such as DNA, within the cell. Ionizing radiation-induced DNA breaks represent one of the dominant mechanisms of action of beta brachytherapy.

Multiple pathways are involved in the cell after its exposure to ionizing radiation. In the cellular response to radiation, several sensors detect the induced DNA damage and trigger signal transduction pathways. The activation of several signal transduction pathways by ionizing radiation results in altered expression of a series of target genes.

The promoters or enhancers of these genes may contain binding sites for one or more transcription factors, and a specific transcription factor can influence the transcription of multiple genes. The transcription factors p53, nuclear factor κB (NF-κB), the specificity protein 1 (SP1)-related retinoblastoma control proteins (RCPs), two p53 dependent genes, GADD45 and CDKN1A, and genes associated with the NER pathway (e.g., XPC) are typically upregulated by ionizing radiation exposure. Interestingly, NF-κB activation has been shown to strongly depend on charged particles' LET, with a maximal activation in the LET range of 90-300 keV/μm.

Importantly, the transcribed subset of target genes is critical for the decision between resuming normal function after cell-cycle arrest and DNA repair, entering senescence, or proceeding through apoptosis in cases of severe DNA damage.

Arrest of the cell cycle is an important part of DNA damage response, facilitating DNA repair and maintenance of genomic stability. Regulators of cell cycle arrest are activated by phosphorylation by ataxia telangiectasia mutated (ATM) and ATR. For example, p53 has a short half-life and is stabilized in response to a variety of cellular stresses after phosphorylation by ATM. After exposure to ionizing radiation, phosphorylation of the serine residues 15 and 20 on p53 by checkpoint kinase 2 (CHK2) reduces its binding to MDM2, which in its bound state targets p53 for degradation by the proteasome pathway. Thus, dissociation of p53 from MDM2 prolongs the half-life of p53. Other proteins, such as Pin 1, Parc, and p300, and p300/CBP-associated factor (PCAF) histone acetyltransferases regulate the transactivation activity of p53. For efficient repair, especially in non-dividing cells, cellular levels of deoxyribonucleotides are increased during the DNA damage repair by p53-dependent transcriptional induction of the ribonucleotide reductase RRM2B (p53R2). It is accepted that the severity of DNA damage is the critical factor in directing the signaling cascade toward reversible cell cycle arrest or apoptosis. As part of the signaling cascade, the abundance of p53 protein, specific posttranslational modifications, and its interaction with downstream effectors, such as GADD45α or p21, may be responsible for directing the cellular response at this decision point.

Other pathways besides DNA and p53 can be involved in the cellular response to exposure to ionizing radiation. For example, ionizing radiation can produce reactive oxygen species (ROS) in the cytoplasm.

Low-dose radiotherapy (LD-RT) is known to exert an anti-inflammatory effect. In vitro models have revealed anti-inflammatory effects of LD-RT in doses ranging from 0.1-1.0 Gy on immune cells such as macrophages and neutrophils. Studies have also shown that low-dose radiation therapy has an anti-inflammatory effect involving diminished CCL20 chemokine expression and granulocyte/endothelial cell adhesion. An in vitro study by Khaw et al. (1991, British Journal of Ophthalmology 75:580-583) of beta irradiation of fibroblasts in culture found that "radiation reduces the proliferation of human Tenon's capsule fibroblasts. The doses of radiation which inhibited cell proliferation more than 50% (at day 7 and 14) and yet did not cause a decrease in the cell population were 500, 750, and 1000 rads." The fibroblasts enter a period of growth arrest but do not die.

The present invention features systems and devices for the application of beta radiation used in combination with surgical procedures and/or implants (e.g., MIGS implants) as described herein. The brachytherapy provided by the systems and devices herein helps to prevent or reduce bleb scarring or failure to maintain a functioning bleb. Without wishing to limit the present invention to any theory or mechanism, it is believed that the brachytherapy devices and systems herein may help to inhibit or reduce inflammation and/or fibrogenesis by downregulating cellular (e.g., fibroblast) activity without cell death.

The application of beta radiation provides a medicament-like treatment, similar to a drug, wherein the beta radiation, when consumed by the cells, causes biological changes in signaling and gene transcription, thereby affecting cellular activity and growth, e.g., cell cycle arrest.

The present invention provides compositions or products that are radioactive compositions (sources of beta radiation). The radioactive composition has a therapeutic effect via the generation of beta radiation by, for example, the mechanisms previously discussed. In generating the beta radiation, radioactive composition is consumed (e.g., the product is gradually used up), in that the radioisotope atoms of the beta radioisotope brachytherapy source decay into other nuclides.

Targets of the Eye

As previously discussed, the present invention provides systems and devices, e.g., ophthalmic applicator systems, brachytherapy systems, etc., for applying beta radiation, e.g., to a treatment area or target of the eye. In some embodiments, the target is a site of the bleb in an eye being treated for glaucoma with a MIGS implant or MIGS procedure. In some embodiments, the target is a site of the bleb in an eye treated with a trabeculectomy. In some embodiments, the target is a site of the bleb in an eye treated with minimally invasive micro sclerostomy (MIMS). In some embodiments, the target is a site of the hole in an eye treated with MIMS. In some embodiments, the target is a site of the implant that is surgically inserted into the eye for the purpose of treating glaucoma. In some embodiments, the target is a site of the eye associated with pterygium.

In some embodiments, the target area is the entire bleb, e.g., the perimeter of the bleb, the center of the bleb, and the portions of the bleb in between the perimeter and the center. In some embodiments, the target area is the perimeter of the bleb, e.g., a ring-shaped target area. In some embodiments, the target is the perimeter of the bleb and a portion of the bleb next to the perimeter, e.g., the target may be annulus-shaped. In some embodiments, the target is a portion of the bleb in between the center and the perimeter. In some embodiments, the target is at least a portion of the center of the bleb. The present invention is not limited to the aforementioned descriptions of target areas. For example, in certain embodiments, the target is (or includes) tissue surrounding the rim of a drainage channel.

In some embodiments, the target is a target other than that associated with MIGS/MIMS/trabeculectomy. In some embodiments, the ophthalmic target is other targets than those associated with glaucoma drainage surgery. In some embodiments the target is inflammation, autoimmune mediated pathologies, or vascular pathologies of the eye. In some embodiments, the target is associated with infections (for example, Herpes Simplex Keratitis or Tuberculous sclero-keratitis), Corneal ulcerations (for example, Moorens), Allergic disorders (for example, Vernal), benign or malignant Tumors (for example, Squamous Cell Carcinoma) or benign growths (for example, papillomas), Degenerations (for example, pterygium), Cicitarising disease (for example, pemphigoid), Inflammations (for example, meibomian gland), ocular manifestations of Stevens-Johnson syndrome, Drug-induced cicatrizing conjunctivitis, Ligneous conjunctivitis, Corneal Vascularization, Pterygia, Vernal Catarrh, Small papillomas of the eyelid, limbal carcinoma, ocular malignant melamona, nevus pigmentosus of the conjunctiva, hemangioma, chalazion. In some embodiments, the target is in the orbit of the eye. The present invention includes other ophthalmic indications and is not limited to the aforementioned targets.

Brachytherapy Systems and Devices

The brachytherapy systems and devices of the present invention may comprise (a) a cap system for accepting a radionuclide brachytherapy source (RBS); (b) a cap system and an RBS; (c) a cap system and an applicator (e.g., a handle); (d) a cap system, an RBS, and an applicator (e.g., a handle); (e) a cap system and a radiation attenuation shield; (f) a cap system, an RBS, and an radiation attenuation shield; (g) a cap system, a radiation attenuation shield, and an applicator (e.g., a handle); (h) a cap system, an RBS, radiation attenuation shield, and an applicator (e.g., a handle); or (i) any other combination of components described herein.

(A) Radionuclide Brachytherapy Source (RBS)

The RBS of the present invention is constructed in a manner that is consistent with the Federal Code of Regulations, but is not limited to the terms mentioned in the Code. For example, the RBS of the present invention may further comprise a substrate. Also, for example, in addition to being enclosed by the mentioned "gold, titanium, stainless steel, or platinum", in some embodiments the radionuclide (isotope) of the present invention may be enclosed by a combination of one or more of "gold, titanium, stainless steel, or platinum". In some embodiments, the radionuclide (isotope) of the present invention may be enclosed by one or more layers of an inert material comprising silver, gold, titanium, stainless steel, platinum, tin, zinc, nickel, copper, other metals, ceramics, glass, or a combination of these.

In some embodiments, the radioisotope comprises Strontium-90 (Sr-90), Phosphorus-32 (P-32), Ruthenium 106 (Ru-106), Yttrium 90 (Y-90), or a combination thereof. In some embodiments, the source of beta radiation comprises Strontium-90 (Sr-90), Phosphorus-32 (P-32), Ruthenium 106 (Ru106), Yttrium 90 (Y-90), or a combination thereof. As an example, the RBS may comprise Strontium-90Y/trium-90, sealed in a disk-shaped capsule of stainless steel or titanium, although other appropriate radioisotopes and other appropriate capsule materials can be used. In some embodiments, the RBS is fixedly attached to the brachytherapy system. In some embodiments, the RBS is removably engaged in the brachytherapy system. In some embodiments, the RBS is engaged or loaded in the brachytherapy system prior to use.

In some embodiments, the RBS comprises a substrate, a radioactive isotope (e.g., Sr-90, Y-90, Rh-106, P-32, etc.), and an encapsulation, enclosing the substrate and isotope. In some embodiments, the isotope is coated on the substrate, and both the substrate and isotope are further coated with the encapsulation. In some embodiments, the radioactive isotope is embedded in the substrate. In some embodiments, the radioactive isotope is part of the substrate matrix. In some embodiments, the encapsulation may be coated onto the isotope, and optionally, a portion of the substrate. In some embodiments, the encapsulation is coated around the entire substrate and the isotope. In some embodiments, the radioactive isotope is an independent piece and is sandwiched between the encapsulation and the substrate. The present invention is not limited to the aforementioned RBS configurations.

In some embodiments, a surface on the substrate is shaped in a manner to provide a controlled projection of radiation. The substrate may be constructed from a variety of materials. For example, in some embodiments the substrate is constructed from a material comprising, a silver, an aluminum, a stainless steel, tungsten, nickel, tin, zirconium, zinc, copper, a metallic material, a ceramic material, a ceramic matrix, the like, or a combination thereof. In some embodiments, the substrate functions to shield a portion of the radiation emitted from the isotope. The encapsulation may be constructed from a variety of materials, for example from one or more layers of an inert material comprising a steel, a silver, a gold, a titanium, a platinum, another bio-compatible material, the like, or a combination thereof.

Figure 1B:
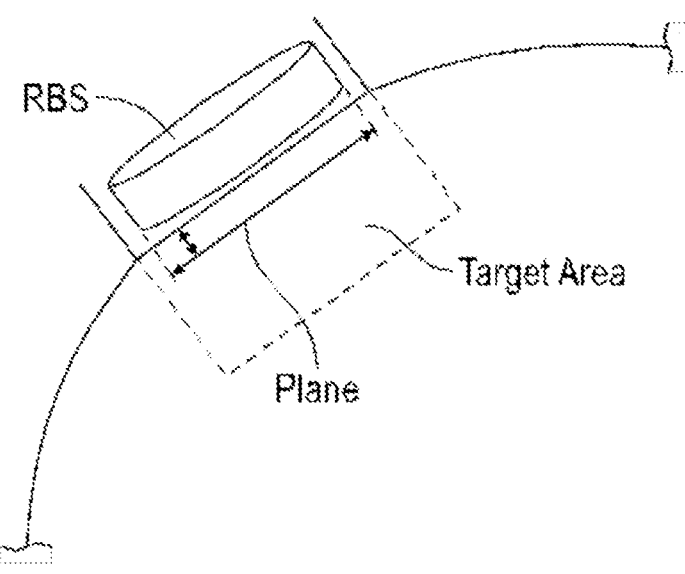
FIG. 1B shows a schematic view of a plane within a treatment area.

Without wishing to limit the present invention to any theory or mechanisms, it is believed that previous brachytherapy sources generally only treated the center part of the target or under-dose the peripheral area and/or over-dose the center (see FIG. 1A). The systems of the present invention generally provide a more uniform dose across the target area, e.g., across a plane within the target area (see FIG. 1A, FIG. 1B). In certain embodiments, the radionuclide brachytherapy source (RBS) may be designed and/or constructed to provide a more substantially uniform radiation dose across a plane within the target, e.g., as compared to previously constructed devices. In certain embodiments, a portion of the brachytherapy system (e.g., cap system, radiation attenuation shield, etc.) may be designed and/or constructed to provide a more substantially uniform radiation dose across the target, e.g., as compared to previously constructed devices. In certain embodiments, a portion of the brachytherapy system (e.g., cap system, radiation attenuation shield, etc.) and the RBS may be designed and/or constructed to provide a more substantially uniform radiation dose across the target, e.g., as compared to previously constructed devices. The present invention is not limited to the dosimetry described herein, such as that shown in FIG. 1A. For example, in some embodiments, the system (e.g., the cap system, the radiation attenuation shield, etc.) is designed such that the dose received at the perimeter of the bleb is higher than that received at the center of the bleb.

Iterative computer simulations of output dosimetry may be used to determine an optimized design of a device (e.g., an optimized design of the RBS and/or cap and/or radiation attenuation shield, etc.). Film dosimetry is a method of measuring radioactive delivery from a source and can be used to measure the dose across the target. It can also be used to calibrate or compare radioactive sources or to determine the homogeneity of the dose pattern.

The RBS may be disc shaped or have an annulus or rounded shape; however, the present invention is not limited to those shapes, and any shape that achieves a desired dose profile is encompassed herein. The shape of the RBS may help provide a controlled projection of radiation (e.g., a therapeutic dose) onto the target. The shape of the RBS may help the radiation dose to fall off quickly at the periphery of the target (whatever the target is determined to be, e.g., the whole bleb, a portion of the bleb, etc.). This may help keep the radiation within a limited area/volume and may help prevent unwanted exposure of structures such as the lens to radiation.

In some embodiments, the RBS has a diameter from 4 to 20 mm. In some embodiments, the RBS has a diameter from 5 to 15 mm. In some embodiments, the RBS has a diameter from 10 to 20 mm. In some embodiments, the RBS has a diameter from 10 to 15 m. In some embodiments, the RBS has a diameter from 5 to 7 mm (e.g., 5 mm, 6 mm, 7 mm). In some embodiments, the RBS has a diameter from 7 to 10 mm (e.g., 7 mm, 7.5 mm, 8 mm, 8.5 mm, 9 mm, 9.5 mm, 10 mm). In some embodiments, the RBS has a diameter from 9 to 12 mm (e.g., 9 mm, 9.5 mm, 10 mm, 10.5 mm, 11 mm, 11.5 mm, 12 mm). In some embodiments, the RBS has a diameter from 10 to 14 mm (e.g., 10 mm, 10.5 mm, 11 mm, 11.5 mm, 12 mm, 12.5 mm, 13 mm, 13.5 mm, 14 mm). In some embodiments, the RBS has a diameter from 12 to 16 mm (e.g., 12 mm, 12.5 mm, 13 mm, 13.5 mm, 14 mm, 14.5 mm, 15 mm, 15.5 mm, 16 mm). In some embodiments, the RBS has a diameter from 14 to 18 mm (e.g., 14 mm, 14.5 mm, 15 mm, 15.5 mm, 16 mm, 16.5 mm, 17 mm, 17.5 mm, 18 mm). In some embodiments, the RBS has a diameter of 3 mm. In some embodiments, the RBS has a diameter of 4 mm. In some embodiments, the RBS has a diameter of 5 mm. In some embodiments, the RBS has a diameter of 5 mm. In some embodiments, the RBS has a diameter of 6 mm. In some embodiments, the RBS has a diameter of 7 mm. In some embodiments, the RBS has a diameter of 8 mm. In some embodiments, the RBS has a diameter of 9 mm. In some embodiments, the RBS has a diameter of 10 mm. In some embodiments, the RBS has a diameter of 11 mm. In some embodiments, the RBS has a diameter of 12 mm. In some embodiments, the RBS has a diameter of 13 mm. In some embodiments, the RBS has a diameter of 14 mm. In some embodiments, the RBS has a diameter of 15 mm. In some embodiments, the RBS has a diameter of 16 mm. In some embodiments, the RBS has a diameter of 17 mm. In some embodiments, the RBS has a diameter of 18 mm. In some embodiments, the RBS has a diameter of 19 mm. In some embodiments, the RBS has a diameter of 20 mm. In some embodiments, the RBS has a diameter more than 20 mm.

The system delivers a particular radiation dose to the target, e.g., to a plane within the target (e.g., a plane of a certain size representing a portion of the treatment area (e.g., PTV)). In some embodiments, the system delivers a radiation dose of 1000 cGy (10 Gy) to the target. In some embodiments, the system delivers a radiation dose of 900 cGy to the target. In some embodiments, the system delivers a radiation dose of 800 cGy to the target. In some embodiments, the system delivers a radiation dose of 750 cGy to the target. In some embodiments, the system delivers a radiation dose of 600 cGy to the target. In some embodiments, the system delivers a radiation dose of 500 cGy to the target. In some embodiments, the system delivers a radiation dose of 400 cGy to the target. In some embodiments, the system delivers a radiation dose of 300 cGy to the target. In some embodiments, the system delivers a radiation dose of 200 cGy to the target. In some embodiments, the system delivers a radiation dose of 100 cGy to the target. In some embodiments, the system delivers a radiation dose of 50 cGy to the target. In some embodiments, the system delivers a radiation dose of 1100 cGy to the target. In some embodiments, the system delivers a radiation dose of 1200 cGy to the target. In some embodiments, the system delivers a radiation dose of 1300 cGy to the target. In some embodiments, the system delivers a radiation dose of 1500 cGy to the target. In some embodiments, the system delivers a radiation dose from 600 cGy and 1500 cGy to the target. In some embodiments, the system delivers a radiation dose from 50 cGy to 100 cGy. In some embodiments, the system delivers a radiation dose from 100 cGy to 150 cGy. In some embodiments, the system delivers a radiation dose from 150 cGy to 200 cGy. In some embodiments, the system delivers a radiation dose from 200 cGy to 250 cGy. In some embodiments, the system delivers a radiation dose from 250 cGy to 300 cGy. In some embodiments, the system delivers a radiation dose from 300 cGy to 350 cGy. In some embodiments, the system delivers a radiation dose from 350 cGy to 400 cGy. In some embodiments, the system delivers a radiation dose from 400 cGy to 450 cGy. In some embodiments, the system delivers a radiation dose from 450 cGy to 500 cGy. In some embodiments, the system delivers a radiation dose from 500 cGy to 550 cGy. In some embodiments, the system delivers a radiation dose from 550 cGy to 600 cGy. In some embodiments, the system delivers a radiation dose from 600 cGy to 650 cGy. In some embodiments, the system delivers a radiation dose from 650 cGy to 700 cGy. In some embodiments, the system delivers a radiation dose from 700 cGy to 750 cGy. In some embodiments, the system delivers a radiation dose from 750 cGy to 800 cGy. In some embodiments, the system delivers a radiation dose from 800 cGy to 850 cGy. In some embodiments, the system delivers a radiation dose from 850 cGy to 900 cGy. In some embodiments, the system delivers a radiation dose from 900 cGy to 950 cGy. In some embodiments, the system delivers a radiation dose from 950 cGy to 1000 cGy. In some embodiments, the system delivers a radiation dose from 1000 cGy to 1050 cGy. In some embodiments, the system delivers a radiation dose from 1050 cGy to 1100 cGy. In some embodiments, the system delivers a radiation dose from 1100 cGy to 1150 cGy. In some embodiments, the system delivers a radiation dose from 1150 cGy to 1200 cGy. In some embodiments, the system delivers a radiation dose from 1200 cGy to 1250 cGy. In some embodiments, the system delivers a radiation dose from 1250 cGy to 1300 cGy. In some embodiments, the system delivers a radiation dose from 1300 cGy to 1350 cGy. In some embodiments, the system delivers a radiation dose from 1350 cGy to 1400 cGy. In some embodiments, the system delivers a radiation dose from 1400 cGy to 1450 cGy. In some embodiments, the system delivers a radiation dose from 1450 cGy to 1500 cGy. In some embodiments, the system delivers a radiation dose from 1500 cGy to 1550 cGy. In some embodiments, the system delivers a radiation dose from 1550 cGy to 1600 cGy. In some embodiments, the system delivers a radiation dose from 1600 cGy to 1800 cGy. In some embodiments, the system delivers a radiation dose from 1800 cGy to 2000 cGy. In some embodiments, the system delivers a radiation dose of 600, 650, 700, 750, 800, 850, 900, 950, 1000, 1050, 1100, 1150, 1200, 1250, 1300, 1350, 1400, 1450, or 1500 cGy to the target. In some embodiments, the system delivers a radiation dose of 1500 to 3200 cGy. In some embodiments, the system delivers a radiation dose of 3200 to 8000 cGy. In some embodiments, the system delivers a radiation dose of 8000 cGy to 10000 cGy. In some embodiments, the system delivers a radiation dose of greater than 10000 cGy.

In some embodiments, the system provides a dose of beta radiation to the target (e.g., a plane of a particular size/diameter within the treatment area), wherein the dose at any point on the target (e.g., a plane of a particular size/diameter within the treatment area) is within 10% of a dose at any other point on the target. In some embodiments, the system provides a dose of beta radiation to the target (e.g., a plane of a particular size/diameter within the treatment area), wherein the dose at any point on the target (e.g., a plane of a particular size/diameter within the treatment area) is within 20% of a dose at any other point on the target. In some embodiments, the system provides a dose of beta radiation to the target (e.g., a plane of a particular size/diameter within the treatment area), wherein the dose at any point on the target (e.g., a plane of a particular size/diameter within the treatment area) is within 30% of a dose at any other point on the target.

In some embodiments, the system (e.g., cap system, radiation attenuation shield, etc.) is designed such that the dose received at the perimeter of the bleb is similar to that at the center, e.g., not less than 80% of the dose of the center, not less than 90% of the dose at the center, etc. In some embodiments, the system (e.g., cap system, radiation attenuation shield, etc.) is designed such that any point of the target is within 20% of the dose of any other point of the target, e.g., the variation of dose across the target is not more than 20%, e.g., at any given point the variation is not more than 20%. In some embodiments, the system (e.g., cap system, radiation attenuation shield, etc.) is designed such that any point of the target is within 15% of the dose of any other point of the target, e.g., the variation of dose across the target is not more than 15%, e.g., at any given point the variation is not more than 15%. In some embodiments, the system (e.g., cap system, radiation attenuation shield, etc.) is designed such that any point of the target is within 10% of the dose of any other point of the target, e.g., the variation of dose across the target is not more than 10%, e.g., at any given point the variation is not more than 10%. In some embodiments, the system (e.g., cap system, radiation attenuation shield, etc.) is designed such that any point of the target is within 8% of the dose of any other point of the target, e.g., the variation of dose across the target is not more than 8%, e.g., at any given point the variation is not more than 8%. In some embodiments, the system (e.g., cap system, radiation attenuation shield, etc.) is designed such that any point of the target is within 5% of the dose of any other point of the target, e.g., the variation of dose across the target is not more than 5%, e.g., at any given point the variation is not more than 5%. In some embodiments, the system (e.g., cap system, radiation attenuation shield, etc.) is designed such that any point of the target is within 3% of the dose of any other point of the target, e.g., the variation of dose across the target is not more than 3%, e.g., at any given point the variation is not more than 3%.

In some embodiments, the system delivers the prescribed dose in a time from 10 seconds to 20 minutes. In some embodiments, the system delivers the prescribed dose in a time from 20 seconds and 10 minutes. In some embodiments, the system delivers the prescribed dose in a time from 20 seconds to 60 seconds. In some embodiments, the system delivers the prescribed dose in a time from 30 seconds to 90 seconds. In some embodiments, the system delivers the prescribed dose in a time from 60 seconds to 90 seconds. In some embodiments, the system delivers the prescribed dose in a time from 90 seconds to 2 minutes. In some embodiments, the system delivers the prescribed dose in a time from 2 minutes to 3 minutes.

In some embodiments, the system delivers the prescribed dose in a time from 3 minutes to 4 minutes. In some embodiments, the system delivers the prescribed dose in a time from 3 minutes to 5 minutes. In some embodiments, the system delivers the prescribed dose in a time from 3 minutes to 6 minutes. In some embodiments, the system delivers the prescribed dose in a time from 4 minutes to 5 minutes. In some embodiments, the system delivers the prescribed dose in a time from 4 minutes to 6 minutes. In some embodiments, the system delivers the prescribed dose in a time from 5 minutes to 6 minutes. In some embodiments, the system delivers the prescribed dose in a time from 6 minutes to 7 minutes. In some embodiments, the system delivers the prescribed dose in a time from 7 minutes to 8 minutes. In some embodiments, the system delivers the prescribed dose in a time from 8 minutes to 9 minutes. In some embodiments, the system delivers the prescribed dose in a time from 9 minutes to 10 minutes. In some embodiments, system delivers the prescribed dose in a time from 10 minutes to 12 minutes. In some embodiments, the system delivers the prescribed dose in a time from 12 minutes to 15 minutes. In some embodiments, the system delivers the prescribed dose in a time from 15 minutes to 20 minutes.

In some embodiments, the system delivers the prescribed dose within 5 seconds. In some embodiments, the system delivers the prescribed dose within 10 seconds. In some embodiments, the system delivers the prescribed dose within 15 seconds. In some embodiments, the system delivers the prescribed dose within 20 seconds. In some embodiments, the system delivers the prescribed dose within 25 seconds. In some embodiments, the system delivers the prescribed dose within 45 seconds. In some embodiments, the system delivers the prescribed dose within 60 seconds. In some embodiments, the system delivers the prescribed dose within 90 seconds. In some embodiments, the system delivers the prescribed dose within 2 minutes. In some embodiments, the system delivers the prescribed dose within 3 minutes. In some embodiments, the system delivers the prescribed dose within 4 minutes. In some embodiments, the system delivers the prescribed dose within 5 minutes. In some embodiments, the system delivers the prescribed dose within 6 minutes. In some embodiments, the system delivers the prescribed dose within 7 minutes. In some embodiments, the system delivers the prescribed dose within 8 minutes. In some embodiments, the system delivers the prescribed dose within 9 minutes. In some embodiments, the system delivers the prescribed dose within 10 minutes. In some embodiments, the system delivers the prescribed dose within 11 minutes. In some embodiments, the system delivers the prescribed dose within 12 minutes. In some embodiments, the system delivers the prescribed dose within 13 minutes. In some embodiments, the system delivers the prescribed dose within 14 minutes. In some embodiments, the system delivers the prescribed dose within 15 minutes. In some embodiments, the system delivers the prescribed dose within 16 minutes. In some embodiments, the system delivers the prescribed dose within 17 minutes. In some embodiments, the system delivers the prescribed dose within 18 minutes. In some embodiments, the system delivers the prescribed dose within 19 minutes. In some embodiments, the system delivers the prescribed dose within 20 minutes. In some embodiments, the system delivers the prescribed dose in a time frame greater than 20 minutes.

In some embodiments, a dose (e.g., a prescribed dose) may be delivered in a single application. In other embodiments, a dose (e.g., a prescribed dose) may be fractionated and applied in multiple applications. For example, in some embodiments, radiation (e.g., a prescribed dose) may be applied over the course of 2 applications. In some embodiments, radiation (e.g., a prescribed dose) may be applied over the course of 3 applications. In some embodiments, radiation (e.g., a prescribed dose) may be applied over the course of 4 applications. In some embodiments, radiation (e.g., a prescribed dose) may be applied over the course of 5 applications. In some embodiments, radiation (e.g., a prescribed dose) may be applied over the course of more than 5 applications. In some embodiments, radiation (e.g., a prescribed dose) may be applied over the course of 20 applications. In some embodiments, radiation (e.g., a prescribed dose) may be applied over the course of more than 20 applications.

Each application may deliver an equal sub-dose. In some embodiments, one or more of the sub-doses are different. For example, one or more of the sub-doses may be different so as to increase or decrease with each additional application.

According to one embodiment, a dose of radiation may be applied prior to the treatment procedure, e.g., surgery for implantation of a device, e.g., MIGS device, or other appropriate glaucoma procedure, e.g., MIMS. For example, in some embodiments, a dose of radiation may be applied one or more days prior to a surgery (e.g., insertion of a device, MIMS, etc.). In some embodiments, a dose of radiation may be applied within a 24-hour prior before a surgery (e.g., insertion of a device). In some embodiments, a dose of radiation may be applied just prior to a surgery (e.g., insertion of a device, MIMS, etc.), e.g., 1 hour before, 30 minutes before, 15 minutes before, 5 minutes before 1 minute before, etc. In some embodiments, a dose of radiation may be applied during a procedure, e.g., for implantation of a device. In some embodiments, a dose of radiation may be applied right after a surgery (e.g., implantation of a device (e.g., MIGS device), MIMS, etc.), e.g., within 1 minute, 2 minutes, 3 minutes, 5 minutes, 10 minutes, etc.). In some embodiments, a dose of radiation may be applied before an incision is made into the conjunctiva. In some embodiments, a dose of radiation may be applied after an incision is made into the conjunctiva. In other embodiments, a dose of radiation may be applied after a surgery (e.g., insertion of a device). In some embodiments, a dose of radiation may be applied within a 24-hour period after a surgery (e.g., insertion of a device). In some embodiments, a dose of radiation may be applied within one to two days after a surgery (e.g., insertion of a device). In some embodiments, a dose of radiation may be applied within 2 or more days after a surgery (e.g., insertion of a device). In some embodiments the dose may be applied any time after the glaucoma surgery. In some embodiments, the dose is applied months or years after the glaucoma surgery. For example, a dose may be given to patients that did not receive a dose during surgery but at a future date have scar or needling procedures to break up scar tissue.

(B) Brachytherapy Applicator

The present invention also provides brachytherapy applicators for applying the beta radiation to the target in the eye. In certain embodiments, the applicator may feature the RBS fixedly attached to the applicator. For example, the applicator may be manufactured such that the RBS is integrated into the applicator prior to distribution or surgical use. In some embodiments, the applicator is manufactured to accept the RBS at a later time. For example, the applicator may be manufactured and distributed, and the RBS may be attached to or inserted into the applicator prior to its use in surgery.

The applicator may be constructed from any appropriate material, such as a biocompatible material or a combination of materials. Non-limiting examples of biocompatible materials include, but are not limited to, metals (for example, stainless steel, titanium, gold), ceramics and polymers.

Figure 2:
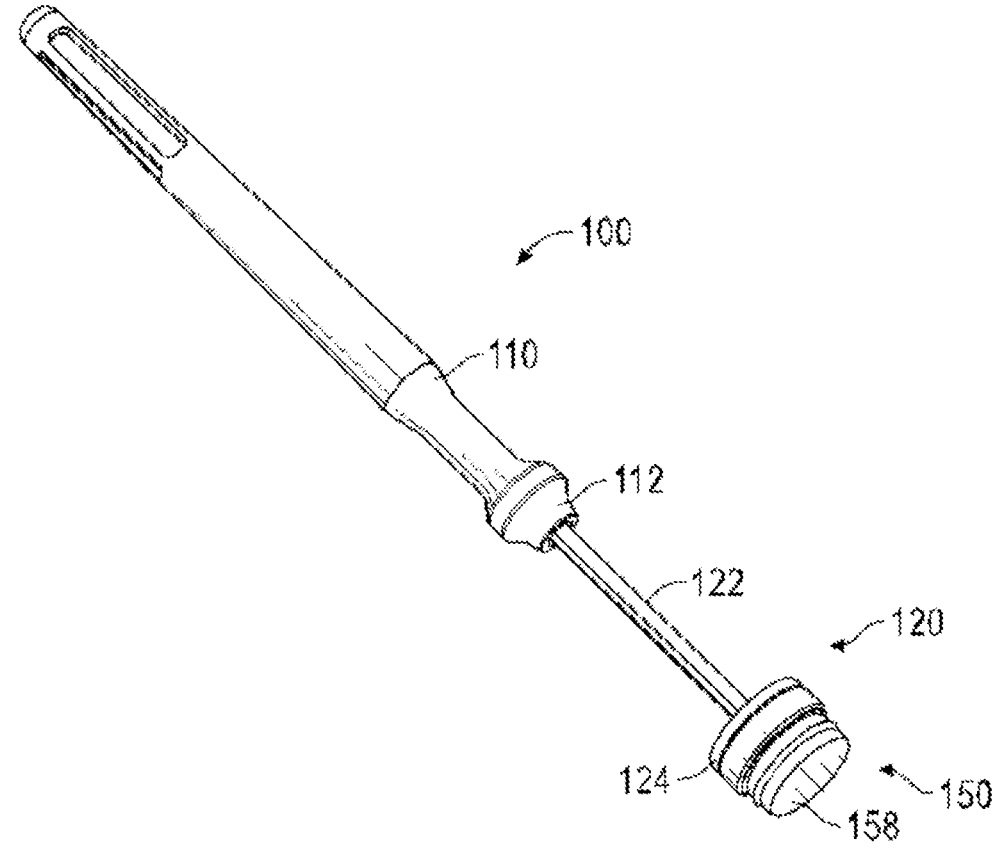
FIG. 2 shows a perspective view of an embodiment of a brachytherapy applicator system of the present invention.
Figure 3:
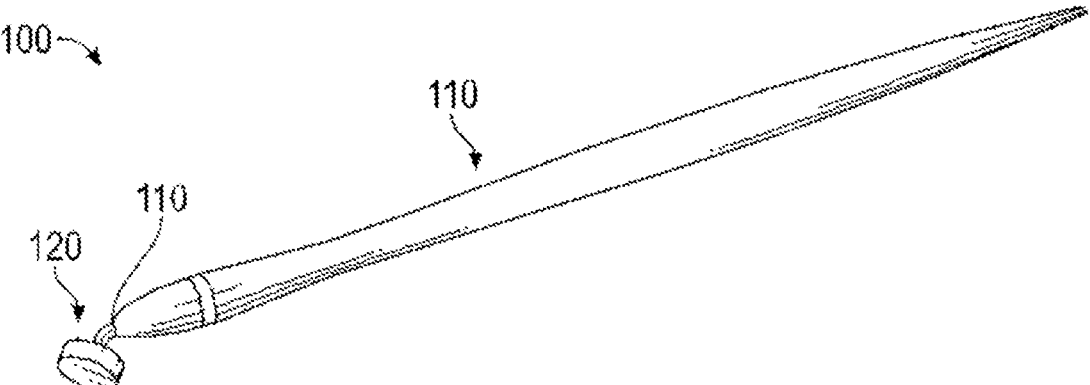
FIG. 3 shows a perspective view of an embodiment of a brachytherapy applicator system of the present invention.

FIG. 2 and FIG. 3 shows a non-limiting example of brachytherapy applicators (100) of the present invention. The applicators (100) comprise a handle (110) and a distal portion (120) at the distal end (112) of the handle (110) for engaging and holding the RBS. The distal portion (120) or a portion thereof may be integrated into (e.g., may be part of) the distal end (112) of the handle (110).

Figure 4A:
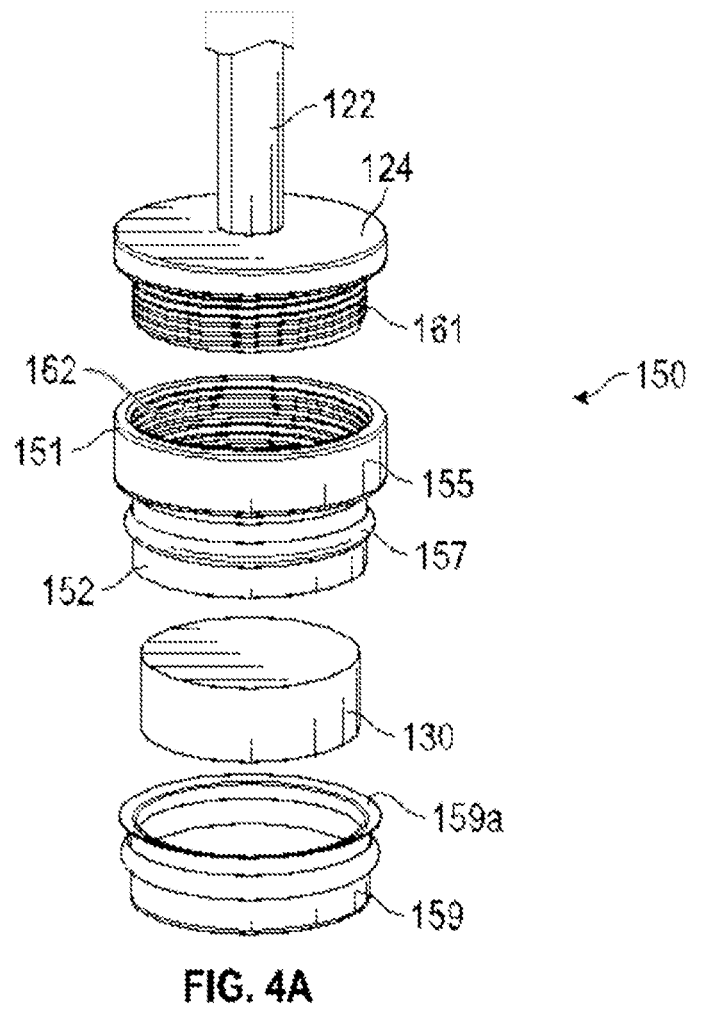
FIG. 4A shows a detailed view of the brachytherapy applicator system of FIG. 2.
Figure 4B:
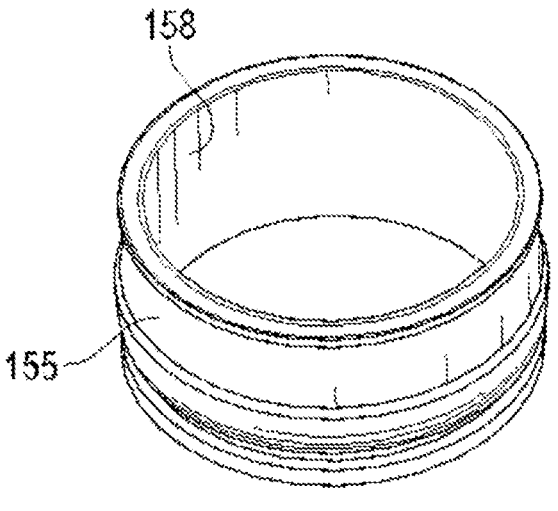
FIG. 4B shows a detailed view of the base ring of the cap system of FIG. 4A.

The distal portion shown in FIG. 2 and FIG. 4A features a stem (122) that is attached to, part of, or capable of engaging the distal end (112) of the handle (110). In some embodiments, the stem (122) is generally straight, e.g., as shown in FIG. 2. In some embodiments, the stem (122) has a curvature.

Attached to the opposite end of the stem (122) (e.g., the end opposite the end that engages the handle (110)) is a disc flange (124). The disc flange (124) engages a cap system (150), which is used for housing and protecting the RBS.

For example, as shown in FIG. 4A, the cap system (150) comprises a base ring (155) for accepting the RBS (130), e.g., a generally cylindrical wall for encircling the RBS (130). The base ring (155) has an open first end (151) for accepting the RBS (130) and a sealed second end (152). The second end (152) of the base ring (155) is sealed by a barrier surface (158), e.g., a surface preventing the RBS (130) from falling through the base ring (155) at the second end (152) (and preventing contact of the RBS with the patient).

The barrier surface (158) may be constructed from a variety of materials. For example, in some embodiments, the barrier surface (158) is constructed from a material comprising a synthetic polymer material (e.g., plastic). The present invention is not limited to a synthetic polymer material (e.g., plastic) for the construction of the barrier surface (158) of the base ring (155). For example, the barrier surface (158) of the base ring (155) may be constructed from a material comprising a metal or metal alloy.

The example shown in FIG. 4A shows a plastic shield (159) that is sealed (e.g., via vacuum, heat, etc.) onto the base ring (155) at the second end (152) in a way that provides a barrier surface (158) for the base ring (155) and wraps around the outer surface of the base ring (155) a distance from the second end (152). In certain embodiments, the outer surface of the base ring (155) comprises a protrusion or ridge (157) and the plastic shield (159) is attached to the base ring (155) such that the top edge (159a) of the plastic shield (159) extends over the ridge (157). This configuration may help prevent the plastic shield (159) from unintentionally sliding off of the base ring (155). The present invention is not limited to the particular plastic shield (159) or fabrication method described herein.

In some embodiments, the disc flange (124) and cap system (150) engage via a threading mechanism. For example, a first thread component (161) may be disposed on the disc flange (124) that is capable of engaging a second thread component (162) disposed on or in the cap system (150), e.g., on or in the base ring (155). The example shown in FIG. 4A shows a first thread component (161) extending downwardly (e.g., in the direction opposite the end of the disc flange (124) that engages the stem (122)) and a second thread component within the top end (122) of the base ring (155), wherein the first thread component (161) is configured to engage the second thread component (162). The present invention is not limited to a male threading component on the disc flange (124) and a female threading component in the base ring (150), e.g., the disc flange (124) may feature a female threading component and the cap system (150) may feature a male threading component.

The present invention is not limited to a threading mechanism for engaging the disc flange (124) and cap system (150). For example, in some embodiments, the disc flange (124) and cap system (150) engage via a snap mechanism or any other appropriate engaging mechanism.

Further, the present invention is not limited to an applicator with a stem (122). (or, in certain embodiments, the stem may be considered part of the distal end (112) of the handle (110)). For example, the applicator system (100) may comprise a handle with a disc flange (124) integrated into or attached to the distal end (112) of the handle (110).

Figures 5, 6, 7:
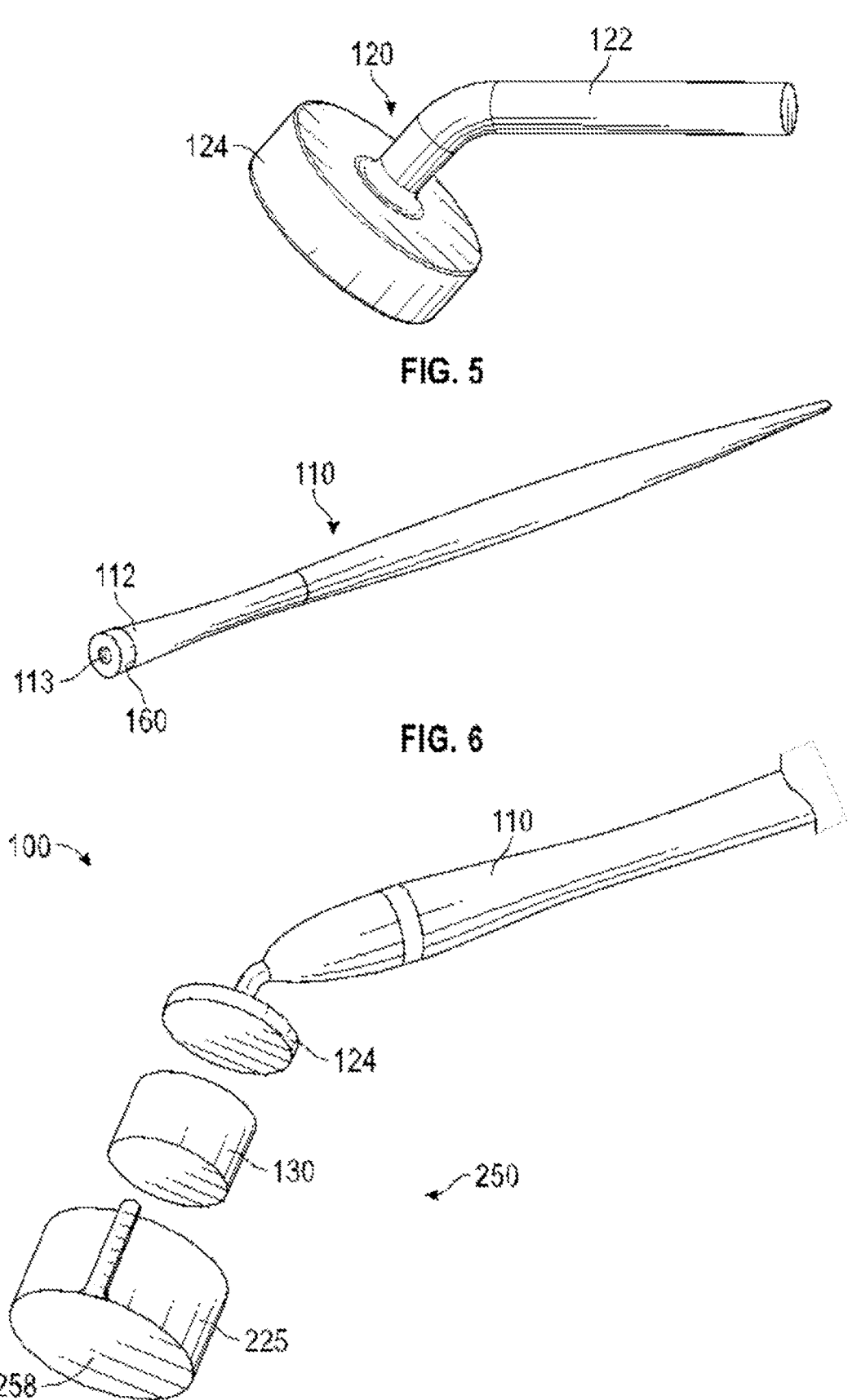
FIG. 5 shows a detailed view of the system of FIG. 3.
FIG. 6 shows a detailed view of the system of FIG. 3.
FIG. 7 shows a detailed view of the system of FIG. 3.

The distal portion (120) shown in FIG. 3 and FIG. 5 features a stem (122) that is attached to, part of, or capable of engaging the distal end (112) of the handle (110). In some embodiments, the stem (122) is generally straight. In some embodiments, the stem (122) has a curvature, e.g., as shown in FIG. 5. A disc flange (124), e.g., a component for engaging an RBS, may be attached to the end of the stem (122) (e.g., the end opposite the end that engages the handle (110)).

In some embodiments, the stem (122) is fixedly attached to the handle (110). In some embodiments, the stem (122) is integrated into the handle (110). In some embodiments, the stem (122) is removably attached to the handle (110). As a non-limiting example, FIG. 6 shows a handle (110) with a shaft or channel (113) disposed in the distal end (112), wherein the channel (113) is for accepting the stem (122) of the distal portion (120).

Referring to FIG. 7 and the embodiment shown in FIG. 3, the system (100) further comprises a cap system (250), which is used for housing and protecting the RBS. The cap system (250) can removably engage the disc flange (124). For example, the cap system (250) shown in FIG. 7 comprises a base ring (255) for accepting an RBS (130). The base ring (255) is a generally cylindrical wall with an open first end for accepting the RBS (130) and a barrier surface (258), creating a sealed second end.

In some embodiments, the cap system (250), e.g., the first end of the base ring (155) has a snap on ridge to allow the base ring (255) to be snapped onto the disc flange (124). In some embodiments, the base ring (255) features a pull-tab for quick release of the barrier surface (258) of the base ring (255) to allow for release of the RBS (130). In some embodiments, the base ring (255) cannot be reused after its release from the applicator (100) (e.g., release from the disc flange (124)). In some embodiments, the base ring (255) helps provide a seal so as to limit fluid access to the RBS and to constrain the RBS.

In some embodiments, the base ring (155, 255) is separate from the RBS (130). In some embodiments, the RBS (130) is integrated into the base ring (155, 255).

The applicator (100), e.g., the handle (110) and/or the distal portion (120), is configured to allow for clear visualization of the treatment and/or the area of the applicator at the interface of the eye (e.g., the applicator-eye interface, the source-eye interface, etc.). In some embodiments, the applicator (100) is shaped similar to the designs shown in FIG. 2 and FIG. 3, wherein the handle (110) has a generally linear configuration. However, the present invention is not limited to the shapes and configurations shown herein. In some embodiments, the handle has a curvature.

The distal portion is not limited to the configurations shown herein. For example, in some embodiments, the distal portion (120) is articulated, e.g., the distal portion (120) can be moved and/or angled as desired.

The handle (110) may feature an ergonomic design, such as that shown in FIG. 2 and FIG. 3, or any other appropriate design. The handle (110) may be designed to allow for extended surgical use, e.g., for comfortably applying radiation to a target for a particular length of time, e.g., a time from 0 to 1 minute, from 1 to 2 minutes, from 2 to 3 minutes, from 3 to 4 minutes, from 4 to 5 minutes, etc.

The length and width of the handle (110), and the length and width of the distal portion (120) (e.g., length of the stem (122), etc.) are not limited to any particular dimensions. However, the length of the handle (110) may be designed to help limit the surgeon's exposure to radiation being emitted from the RBS at the distal end of the applicator (100).

The applicator (100) may further comprise a branding ring (160) or other similar component (e.g., see FIG. 6). The branding ring may be a ring of material, paint, pigment, or other type of marking that distinguishes itself from the handle (110). The branding ring (160) may be used to help the user with alignment of the device. In some embodiments, the branding ring (160) is for design purposes, e.g., for identifying the design with the brand.

Figures 8, 9:
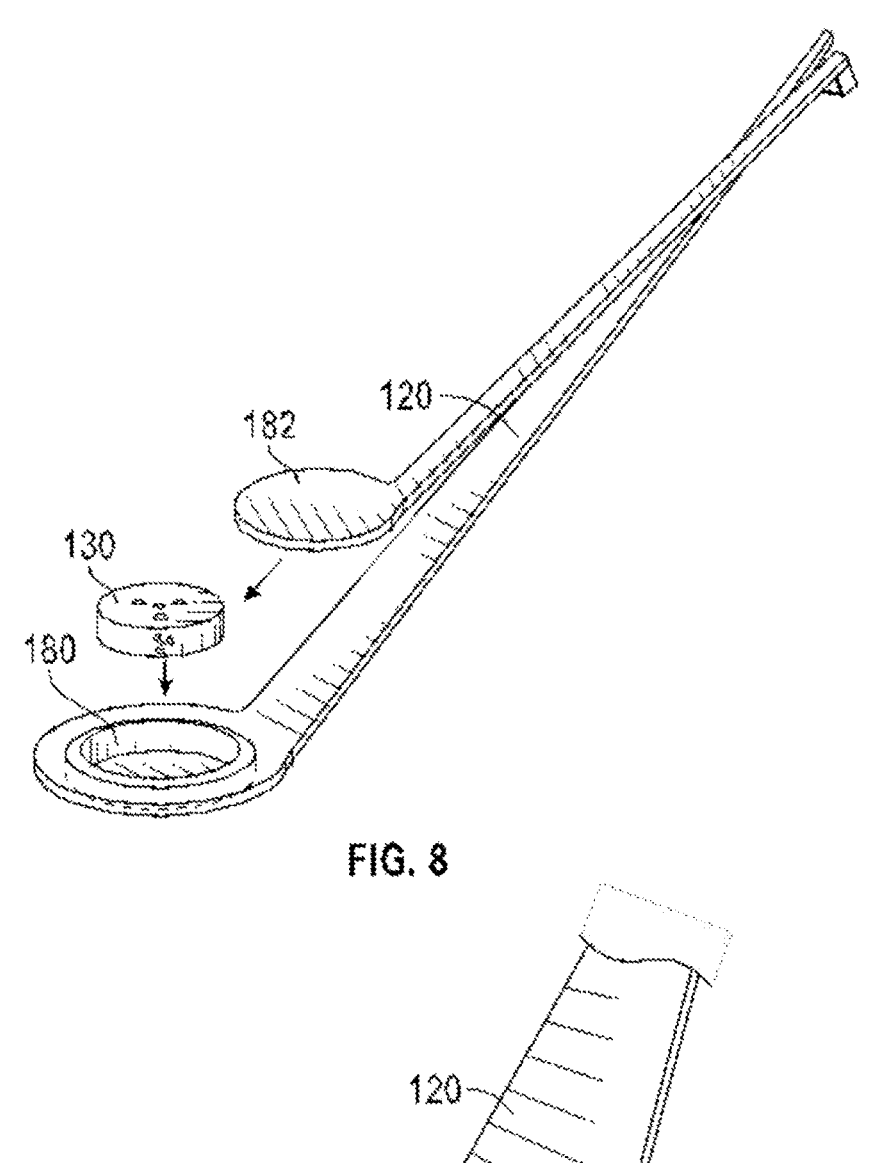
FIG. 8 shows a perspective view of an embodiment of a brachytherapy applicator system of the present invention, wherein an RBS is housed in a well.
FIG. 9 shows a perspective view of an embodiment of a brachytherapy applicator system of the present invention, wherein an RBS is housed in a well.

FIG. 8 and FIG. 9 show alternative embodiments of the system (100) of the present invention. In some embodiments, the distal end of the handle (110) comprises a well (180) for accepting the RBS (130). RBS is contained in a well (150) at the end of the distal portion (120). The handle (110) may further comprise a removable cover (182) for sealing and covering the RBS (130) in the well (180). The cover (182) may be capable of moving between at least an open position (wherein the RBS can be inserted or removed) and a closed position (wherein the RBS is sealed within the well and covered by the cover (182)). As shown in FIG. 8, in certain embodiments, the cover (182) may be slidably attached to the handle (110). In some embodiments, the cover (182) may be removed using a pull tab (not shown). In certain embodiments, the cover (182) is pivotally attached to the handle (see FIG. 9). The cover (182) may be integrated into the handle. FIG. 8 and FIG. 9 show the cover (182) in the open position.

Referring to the well (150) in FIG. 8 and FIG. 9, in some embodiments, the shape of the well (150) helps minimize the movement of the RBS once the RBS is in place in the well (150). The well (150) and cover (182) may provide a seal so as to limit fluid access and constrain the RBS to prevent accidental removal of the RBS. In some embodiments, the well (150) is an integral part of the distal portion of the handle (110). In some embodiments, the well (150) is an integral part of the handle (110).

In some embodiments, the cover (182) works with a locking mechanism to ensure secure containment of the RBS. In some embodiments, the cover (182) snaps on to a flange or handle component. In some embodiments, the cover (182) is part of or comprises a means of releasing the RBS from the well (150), e.g., after a procedure. In some embodiments, the locking mechanism cannot be disengaged (e.g., the RBS released) without destruction of the distal portion of the handle (110), the cap system (150, 250), and/or the cover (182), etc. so as to help prevent accidental release of the RBS and/or reuse of the system (100) and/or cap system (150, 250), and/or cover (182), and/or distal portion (120), etc.

The applicator system (100) of the present invention may feature a source release system (RBS release), e.g., a system for releasing the RBS from the handle (110), e.g., the distal portion (120). In some embodiments, the source release (RBS release) provides a destructive release of a portion of the system (100), e.g., the cap system (150, 250), the cover (182), etc. allowing for the removal of the RBS. In some embodiments, the source release helps ensure the applicator system (100) is for single-use by featuring a destructive mechanism. As a non-limiting example, the release may be a destructive pull tab. In some embodiments, the release may be a destructive twist cap. In some embodiments, the release system is accessible via the handle (110), e.g., a user may be able to activate the release system with a button or level on the handle (110). In some embodiments, the release system is accessible via the distal portion (120).

The cap system, e.g., the barrier surface of the base ring, may be a portion of the interface between the RBS and the surface of the eye. For example, the exterior surface of the barrier surface of the base ring of the cap system may be the portion of the cap system that contacts the eye. Referring to FIG. 10A and FIG. 10B, in some embodiments, the exterior surface (158a) of the barrier surface (158) of the base ring (155) is curved. In certain embodiments, the exterior surface (158a) of the barrier surface (158) of the base ring (155) is generally flat. In certain embodiments, the interior surface (158b) of the barrier surface of the base ring (the surface opposite the exterior surface of the barrier surface) may be curved (see FIG. 10A). In certain embodiments, the interior surface (155b) of the barrier surface of the base ring (the surface opposite the exterior surface of the barrier surface) may be straight (see FIG. 10B). The exterior surface and/or the interior surface of the barrier surface of the base ring may be any appropriate shape or configuration.

In some embodiments, the material and/or shape of the cap system (150) and/or other component that is in direct contact with the eye (e.g., radiation attenuation shield) may modify transmission of the radiation in a shape that is optimized for treatment.

The brachytherapy applicator (100) of the present invention may further comprise a radiation attenuation shield (190) (or beam flattening filter) for shaping the emission of the radiation in a particular manner. For example, the radiation attenuation shield (190) of the present invention helps to modify (e.g., optimize) the beta radiation dose distribution delivered across (and/or through) the surface for treatment (e.g., glaucoma bleb tissues). The radiation attenuation shield (190) may modify the output of radiation so as to provide a substantially uniform dose distribution across the treatment radius. In some embodiments, the radiation attenuation shield (190) may limit the amount of radiation that reaches non-target tissues such as the lens.

As shown in FIG. 11A, the radiation attenuation shield (190) may be separate from the RBS and/or cap system (150). For example, the radiation attenuation shield (190) may be removably attachable to the cap system (150), e.g., to the base ring (155, 255). In certain embodiments, the radiation attenuation shield (190) attaches to the cap system (150) via a snap mechanism. In certain embodiments, the radiation attenuation shield (190) attaches to the cap system (150) via an adhesive mechanism. In certain embodiments, the radiation attenuation shield (190) attaches to the cap system (150) via a magnetic mechanism. The radiation attenuation shield (190) may be attached to the cap system (150) via any appropriate attachment mechanism. For example, in some embodiments, the radiation attenuation shield (190) may be fixedly attached to the cap system (150), e.g., via welding or other permanent attachment mechanism.

Figure 11B:
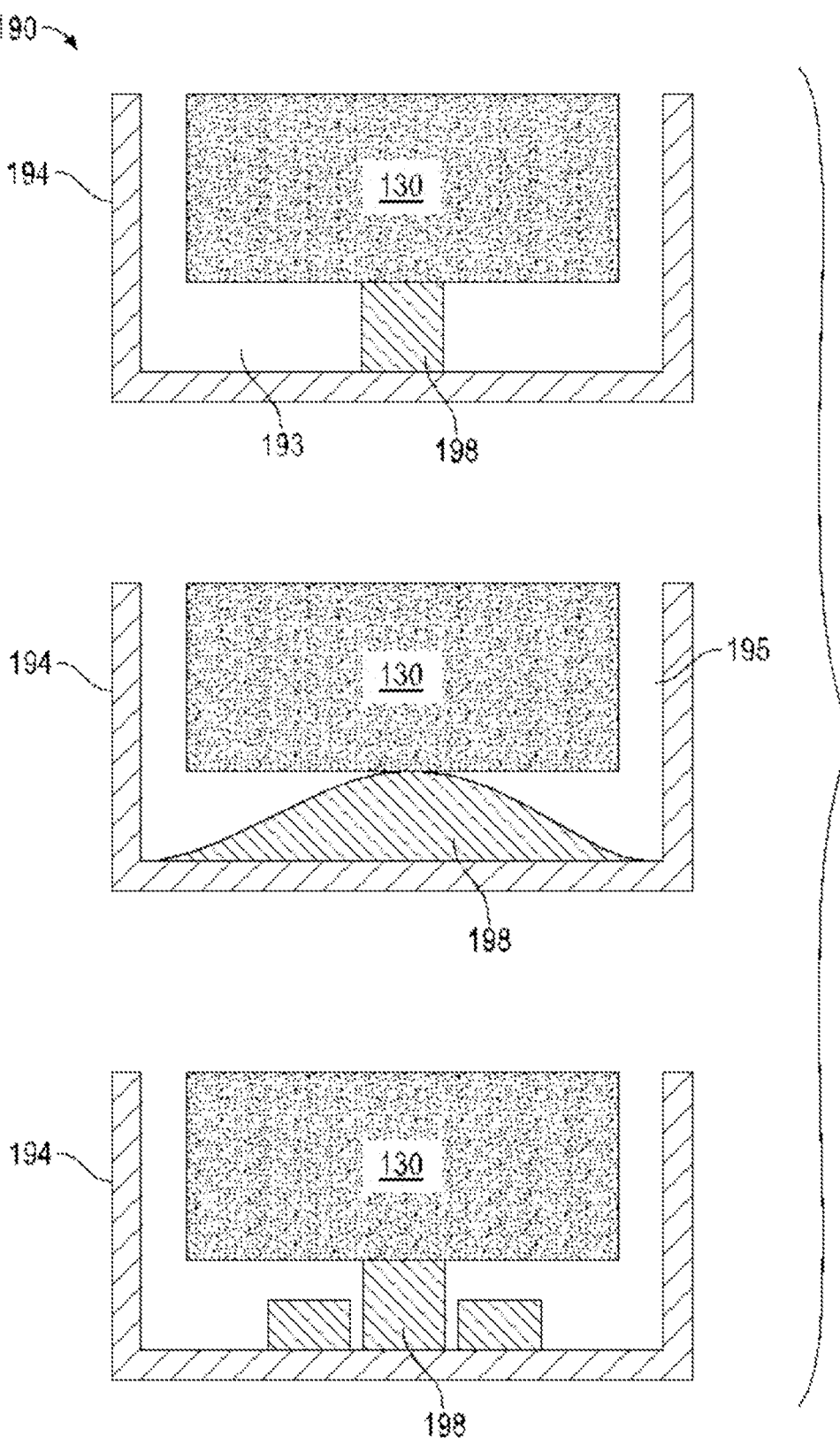
FIG. 11B shows side cross-sectional views of non-limiting examples of radiation attenuation shields. (Cap system not shown.)
Figures 11C, 12:
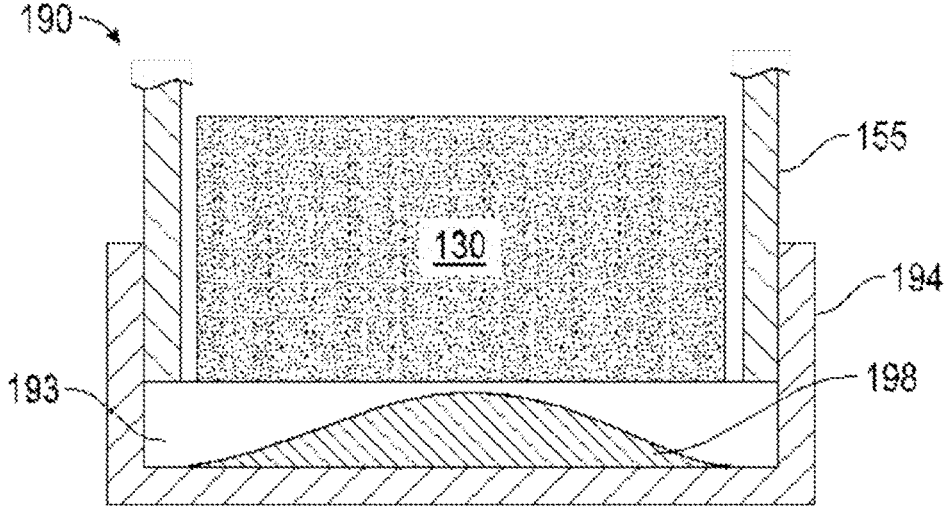
FIG. 11C shows a side cross-sectional view of an example of a radiation attenuation shield attached to a cap system with an RBS.
FIG. 12 shows a schematic view of assembly of an example of a brachytherapy applicator.

FIG. 11A, FIG. 11B, and FIG. 11C show non-limiting examples of radiation attenuation shields (190). The radiation attenuation shield (190) comprises a shield wall (194) with a sealed bottom barrier (193), forming a shield well (195) for accepting the RBS and/or cap system (150). The shield (190) may be generally cylindrical, however the present invention is not limited to a cylindrical shape. The side wall (194) of the shield (190) surrounds at least a portion of the RBS and/or cap system, e.g., as shown in FIG. 11B and FIG. 11C. The shield (190) further comprises a shaping component (198) disposed on the interior surface of the bottom barrier (193) for producing a desired amount and distribution of radiation from the RBS to the exterior surface of the shield (190) (and ultimately the target). In certain embodiments, the shaping component (198) is dome-shaped, e.g., as shown in FIG. 11A, the middle panel of FIG. 11B, and FIG. 11C. The shaping component (198) may be any appropriate shape, size, number of pieces, material, combination of shapes and/or sizes and/or number of pieces and/or materials, etc., that produces the desired amount and distribution of radiation. For example, in certain embodiments, the shaping component (198) is disk shaped. In certain embodiments, the shaping component (198) is rectangular. In some embodiments, the shaping component (198) is a combination of two or more rectangular pieces. In certain embodiments, the shaping component (198) is a foil disc. In certain embodiments, the shaping component (198) is a foil annulus. In certain embodiments, the shaping component (198) is a plastic disc. In certain embodiments, the shaping component (198) is a plastic annulus.

FIG. 11B shows the RBS inserted into the well (195) of the shield (190). FIG. 11C shows the RBS in the cap system (150), e.g., the base ring (155), which is inserted into the well (195) of the shield (190). The present invention is not limited to any of the aforementioned configurations.

In some embodiments, the radiation attenuation shield is integrated into the RBS and/or cap system (150). In some embodiments, the radiation attenuation shield is separate from the RBS and/or cap system.

In some embodiments, the cap system may be combined with an unmasked RBS. In some embodiments the cap system provides the radiation attenuation shield for an optimized dose distribution. In some embodiments both the construction of the RBS with an integrate mask combined with the contribution of the radiation attenuation shield provides the combined attenuation for an optimized dose distribution.

Other permutations are possible. In some embodiments, an unmasked cap can be combined with a masked RBS. In some embodiments an unmasked RBS is combined with an unmasked cap. In some embodiments the radiation attenuation shield is independent of the cap and RBS. In some embodiments a radiation attenuation shield that is separate and independent from the RBS and cap may be combined with an unmasked RBS and unmasked cap, or with any combination of a masked RBS, unmasked RBS, masked cap or unmasked cap.

The radiation attenuation shield is positioned between the radiation source (e.g., RBS) and the target tissue beyond the distal end of the device. In some embodiments the radiation attenuation shield is placed between the RBS and cap. In some embodiments the radiation attenuation shield is placed on the outer surface of the cap.

The radiation attenuation shield may be constructed from one or a variety of materials. In some embodiments, the radiation attenuation shield is constructed from materials of different electron mean free path across its area.

The radiation attenuation shield of the present invention may be designed based on one or a combination of methods, e.g., based on the results of experiments using, in part, film dosimetry experiments. In this method, the density, thickness, diameter, shape and other characteristics of the attenuation material is iteratively modified, and the effect on the distribution of radiation in the target volume can be measured by the optical density of the exposure on radiographic film.

The radiation attenuation shield of the present invention may be designed based on one or a combination of methods, e.g., based on the results of experiments using, in part, Monte Carlo methods. J. E. Gentle, in International Encyclopedia of Education (Third Edition), 2010 "Monte Carlo Methods in Statistics" states that, "Monte Carlo methods are experiments. Monte Carlo experimentation is the use of simulated random numbers to estimate some functions of a probability distribution." In a public presentation by K. Nilsen, PhD, Department of Physics and Scientific Computing Group University of Oslo, N-0316 Oslo, Norway in Spring 2008 "Monte Carlo simulations can be treated as Computer experiments. The results can be analyzed with the same statistics tools we would use in analyzing laboratory experiments." The Los Alamos Monte Carlo N-Particle Transport Code (MCNP) "can be used for neutron, photon, electron, or coupled neutron/photon/electron transport. Specific areas of application include, but are not limited to, radiation protection and dosimetry, radiation shielding, radiography, medical physics, nuclear criticality safety, Detector Design and analysis, nuclear oil well logging, Accelerator target design, Fission and fusion reactor design, decontamination and decommissioning." The "codes can be used to judge whether or not nuclear systems are critical and to determine doses from sources, among other things."

The radiation attenuation shields allow transmission of the radiation in a shape that is optimized for the surgical wound and/or the diameter about that of the bleb. The radiation attenuation shields, in general, have intervening material of various transmissive properties that allow for flattening of the dose across the diameter or over the area. By the same method, attenuation of the radiation can also be achieved by varying the surface output of the beta source so that a portion of the surface has a lower output. By the same method, a uniform dose across the diameter (or a substantially uniform dose across the diameter) can be obtained by the summation of the contributions of varying the surface output of the beta source and masking across the diameter (or area).

The present invention features the design of radiation attenuation shields, and/or the output of the beta source, so that the intended target tissue (e.g., PTV) is best and most fully treated while also limiting stray dose to the lens and other tissues. The beta radiation source and/or radiation attenuation shield output may be optimized to the Planning Treatment Volume(s) specific to the glaucoma drainage procedure bleb or other target area, while also limiting stray dose to the lens and other tissues.

The radiation attenuation shields herein may selectively and variably attenuate the dose across the surface of the radiation attenuation shield. The relative attenuation can be achieved by a number of methods including changes in density, or distance, or variable use of materials and thickness that alter the radiation electron mean free path.

In some embodiments, the applicator features a cover for temporarily shielding the RBS and/or for keeping a portion of the applicator and/or RBS sterile. The cover may be attachable to the RBS. In some embodiments, the cover incorporates a radiation window or mask providing for a substantially uniform dose distribution across the treatment radius. The cover also provides for a sterile barrier between the RBS and the patient.

Previous legacy brachytherapy devices were designed with the intent that the means of application entails the RBS outer casing is applied directly in contact to the surgical site on the anterior eye, often either on the conjunctivae or sclera. Thus, it is interpreted that the devices are applied to the patient without first undergoing formal sterile processing; Rather, the legacy devices are generally cleaned between patient cases with a cloth moistened with alcohol only. For example, the US Nuclear Regulatory Commission documents (Information Notice No. 90-58: US NRC, Sep. 11, 1990) the "Typical Manufacturer's safe handling instructions: Sterilize the applicator by either: (a) immersing the applicator in alcohol in a shielded container, or (b) placing a cotton swab, sponge, or gauze, dampened with a sterilizing agent, on a flat surface and wiping the treatment end of the applicator across the swab, sponge, or gauze, instead of holding it with the finger."

While the radiation emitted from the device gives some added comfort as creating an inhospitable environment for bacteria, this method of cleaning is not consistent with modern regulatory requirements for neither sterility nor absence of pyrogenic material. The present invention features sterilized systems and devices, as well as methods for sterilizing the systems and devices of the present invention consistent with modern regulatory requirements.

In some embodiments, the systems of the present invention provide a sterile barrier placed between the RBS and the patient. In some embodiments, the sterile barrier also attenuates the radiation so as to provide a substantially uniform dose across the relevant treatment area. Thus, in some embodiments, the cap system provides the sterile barrier. In some embodiments, the radiation attenuation shield of the present invention provides the sterile barrier.

In some embodiments, one or more components of the invention (e.g., applicator) are constructed from a material that can further shield the user from the RBS. In some embodiments, a material having a low atomic number (Z) may be used for shielding (e.g., polymethyl methacrylate). In some embodiments, one or more layers of material are used for shielding, wherein an inner layer comprises a material having a low atomic number (e.g., polymethyl methacrylate) and an outer layer comprises lead.

As an example, in some embodiments, the present invention is a device loaded from a Ruthenium-106 cow with an activity of rhodium-106 providing for the prescribed dose. The device can be applied to the target volume to deliver the full activity of its contents. For example, the device may be placed over the target lesion for 10 half-lives (300 seconds), delivering all its radioactive energy and consuming the rhodium-106, depleting it to palladium.

As an example, in some embodiments, the present invention is an applicator constructed containing Strontium-90/Yttrium-90 radioisotopes in secular equilibrium. In some embodiments, the Sr-90/Y-90 is in a sealed source brachytherapy device, e.g., constructed of stainless steel. The source may be constructed to project a dose of about 1,000 cGy per unit time into a sufficient portion of the adjacent Planning Treatment Volume, e.g., to contain the conjunctival tissue to a depth of 0.3 mm. The source may be attached to or integrated into a brachytherapy applicator, and a radiation attenuation shield may be attached to the source or integrated with the source. In some embodiments, the source or attenuation shield or other component may be covered with a sterile barrier. The present invention is not limited to this embodiment, and variations and combinations of the disclosed features are also covered in the scope of this application.

FIG. 12 shows a schematic view of the assembly of a brachytherapy applicator of the present invention. The present invention is not limited to the applicator and the components thereof shown in FIG. 12. The device shown comprises a handle (110) and a distal portion (120). In this example, the distal portion (120) comprises an RBS (130) connected to a stem (122). The handle (110) comprises a shaft (113) for accepting the stem (122) of the distal portion (120). Note the two different distal portions shown, wherein one has a straight stem and one has a curved stem. Also shown is an eye interface cap (260), wherein the outer surface of the second end (262) of the eye interface cap (260) is curved to match the surface of the eye. After the distal portion (120) is attached to the handle (110), the applicator is inserted into the eye interface cap (260) via the first end (261) of the eye interface cap (260). The final image is a fully assembled system.

Figure 13:
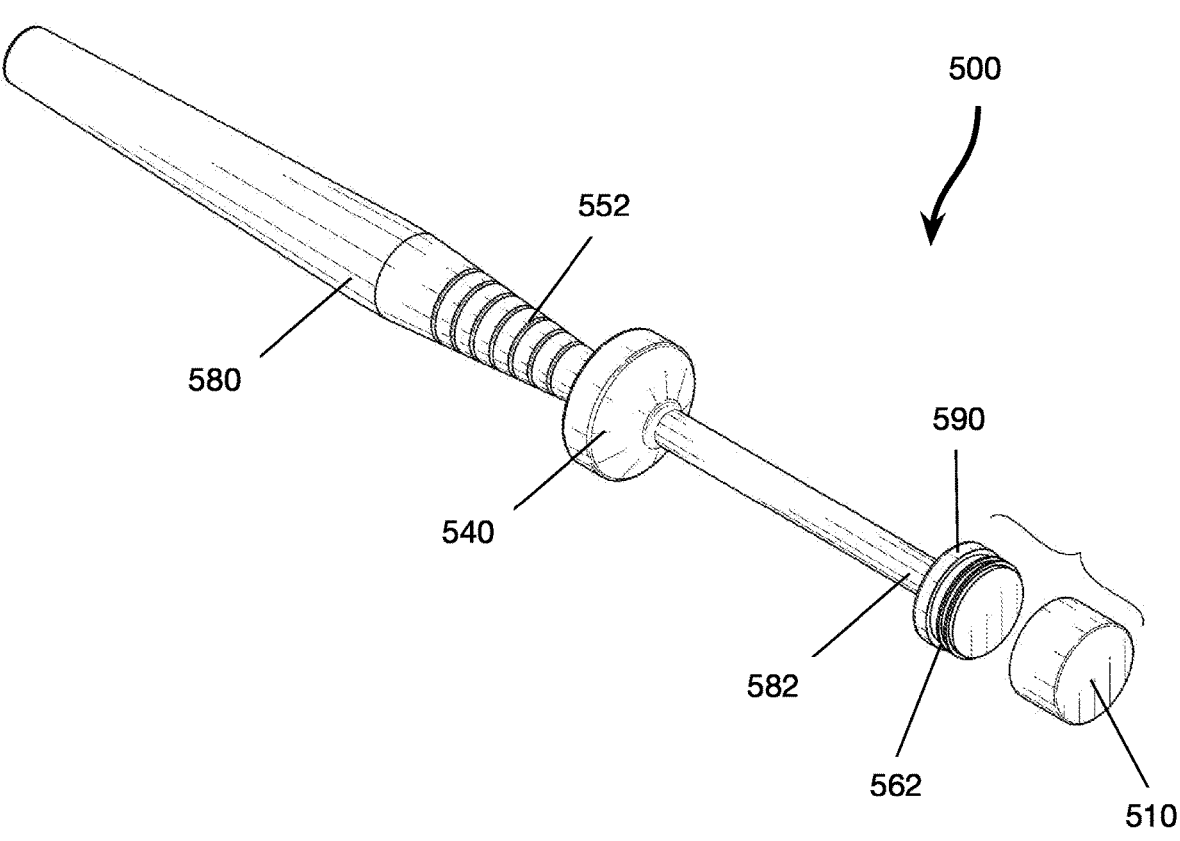
FIG. 13 shows a perspective view of an embodiment of the present invention.
Figure 14:
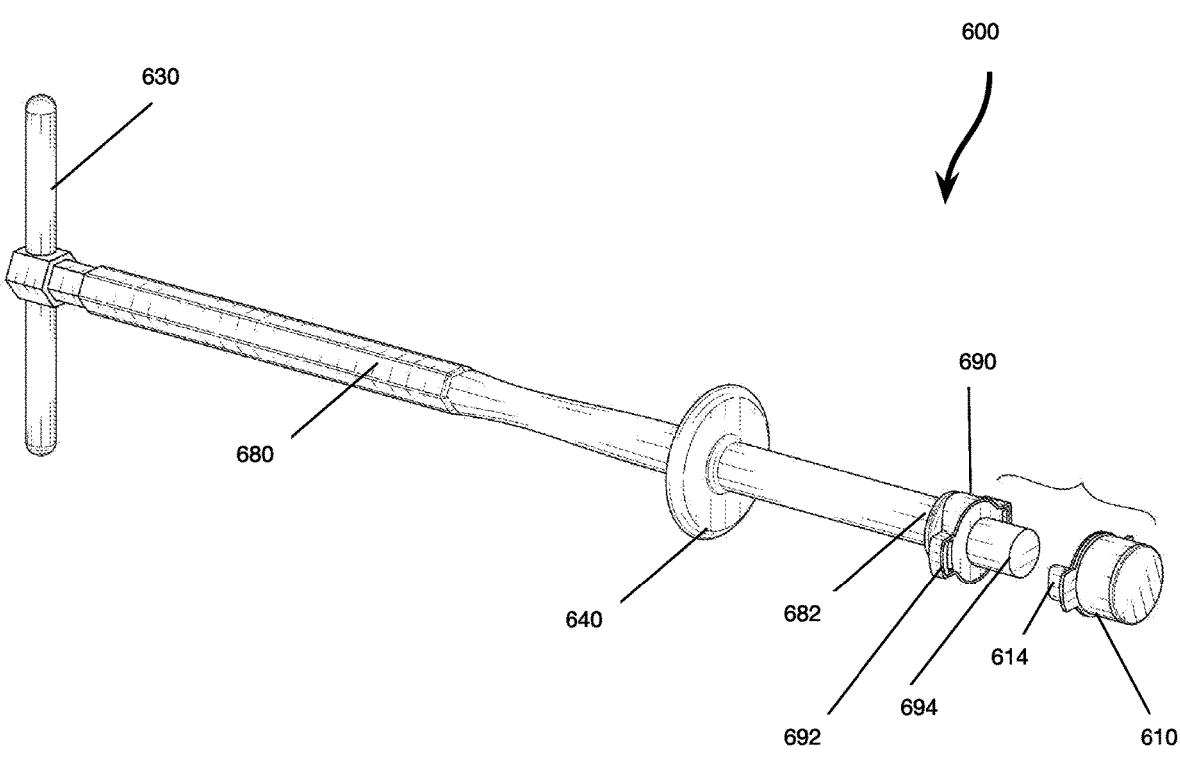
FIG. 14 shows a perspective view of an embodiment of the present invention.

As previously discussed, the present invention provides brachytherapy systems for applying a dose of beta radiation to a target, wherein the systems comprise a handle having a distal end and a cap system attachable (directly or indirectly) to the distal end of the handle. Referring to FIG. 13 and FIG. 14, the cap system may comprise a cylindrical base ring having a first end and a second end opposite the first end and an inner cavity therein for accepting a radionuclide brachytherapy source, wherein the first end is open to allow for insertion of the RBS into the inner cavity; and a barrier surface sealing the second end of the base ring so as to prevent passing of the RBS through the second end. In some embodiments, the cap system further comprises a shaping component disposed on an interior surface of the barrier surface in the inner cavity of the base ring, wherein the shaping component is shaped and constructed to regulate a dose of beta radiation delivered from the RBS to a target plane of a treatment area. As will be shown in FIG. 13, in some embodiments, the cap system and the handle attach (removably) via a threaded mechanism. For example, threads may be disposed on the base ring at the first end (e.g., inside the inner surface of the base ring at the first end, wherein the threads of the cap engage threads disposed on the distal end of the handle. The present invention is not limited to attaching the cap to the handle via a threaded mechanism. For example, in some embodiments, the cap attaches (e.g., removably) to the handle via a snap mechanism.

Referring to FIG. 13, the system (500) may feature a handle (580) having a distal end (582) that engages a cap (510) with an internal cavity for temporarily housing an RBS. For example, an RBS may be inserted into the internal cavity of the cap (510), and the handle (580) may be temporarily attached to or connected to the handle (580).

As shown, the cap (510) features threads (e.g., cap threads) that threadably engage complementary threads (562) disposed on the distal end (582) of the handle (580). In certain embodiments, a handle head (590) is disposed at the distal end (582) of the handle (580), and the complementary threads (562) (e.g., handle threads) are disposed on the handle head (590) as shown in FIG. 13.

In certain embodiments, the handle is not uniform in diameter, e.g., certain portions may have a larger diameter than others. As shown in FIG. 13, the diameter of the handle narrows where the user's fingers grip the handle, as compared to portions of the handle that are more proximal. In certain embodiments, a grip (552) is disposed on the handle. The grip is not limited to any particular configuration, as grips are well known to one of ordinary skill in the art.

Referring to FIG. 13, in some embodiments, the system features a shield (540) disposed on the handle and extending outwardly from the handle. The shield (540) may function to help the user's hand maintain a grip on the appropriate portion of the handle, e.g., help prevent the user's fingers from sliding towards the distal end of the handle. This can help the user maintain the appropriate grip on the handle as well as avoid unnecessary exposure to additional radiation if his/her fingers were too close to the distal end. In some embodiments, the shield (540) may function to block a portion of the radiation that extends backwardly toward user's fingers.

Referring to FIG. 14, the system (600) may feature a handle (680) having a distal end (682) that engages a cap (610) with an internal cavity for temporarily housing an RBS. For example, an RBS may be inserted into the internal cavity of the cap (610), and the handle (680) may be temporarily attached to or connected to the handle (680).

In some embodiments, the cap can attach to the handle (e.g., removably) via a snap mechanism. For example, as shown, in some embodiments, the cap (610) features tabs (614) that protrude upwardly, e.g., in the direction of the handle (e.g., when the handle is attached to the cap (610)). The handle (680) may feature a handle head (690) disposed at the distal end (682) of the handle (680), and the handle head (690) may feature a tab lock (692) that engages the tabs (614) of the cap (610) to secure the cap (610) to the handle (680), e.g., temporarily. In some embodiments, the system features a pair of opposing tabs (614) and tab locks (692).

In some embodiments, the handle head (690) further comprises a stabilizer (694), e.g., an extension of the handle head (690) that extends into the inner cavity of the cap (610) to help stabilize the RBS therein, e.g., to prevent it from moving in the x, y, or z direction.

In certain embodiments, the handle is not uniform in diameter, e.g., certain portions may have a larger diameter than others. For example, the diameter of the handle may narrow where the user's fingers grip the handle, as compared to portions of the handle that are more proximal.

As shown in FIG. 14, the proximal end (581) of the handle (580) may feature a grip (630) that may be used to help attach the cap to the handle or rotate the handle with respect to the cap, e.g., during disassembly. The grip (630) is not limited to the configuration shown in FIG. 14.

Referring to FIG. 14, in some embodiments, the system features a shield (640) disposed on the handle and extending outwardly from the handle. The shield (640) may function to help the user's hand maintain a grip on the appropriate portion of the handle, e.g., help prevent the user's fingers from sliding towards the distal end of the handle. This can help the user maintain the appropriate grip on the handle as well as avoid unnecessary exposure to additional radiation if his/her fingers were too close to the distal end. In some embodiments, the shield (640) may function to block a portion of the radiation that extends backwardly toward the user's fingers.

As previously discussed, the shaping component (198) may be constructed in a variety of shapes as appropriate, e.g., the shaping component (198) may be an annulus, a disc, a rectangle (e.g., square), an ellipse, kidney-shaped, etc. In certain embodiments, the shaping component (198) is generally solid. In certain embodiments, the shaping component (198) comprises one or more pores, e.g., a center hole in the example of an annulus. The present invention is not limited to the aforementioned shapes of shaping components.

Without wishing to limit the present invention to any theory or mechanism, the shaping component of the radiation attenuation shield is designed to attenuate a portion of the beta radiation being emitted from the RBS. For example, in certain embodiments, the shaping component provides a 10-20% attenuation of radiation emitted to at least 50% of the area of the target plane. In certain embodiments, the shaping component provides a 20-50% attenuation of radiation emitted to at least 50% of the area of the target plane. In certain embodiments, the shaping component provides a 30-60% attenuation of radiation emitted to at least 50% of the area of the target plane. In certain embodiments, the shaping component provides a 40-70% attenuation of radiation emitted to at least 50% of the area of the target plane. In certain embodiments, the shaping component provides a 50-75% attenuation of radiation emitted to at least 50% of the area of the target plane.

In certain embodiments, the shaping component provides a 10-20% attenuation of radiation emitted to a portion of the area of the target plane that is from 5-50% of the total area of the target plane. In certain embodiments, the shaping component provides a 20-50% attenuation of radiation emitted to a portion of the area of the target plane that is from 5-50% of the total area of the target plane. In certain embodiments, the shaping component provides a 30-60% attenuation of radiation emitted to a portion of the area of the target plane that is from 5-50% of the total area of the target plane. In certain embodiments, the shaping component provides a 40-70% attenuation of radiation emitted to a portion of the area of the target plane that is from 5-50% of the total area of the target plane. In certain embodiments, the shaping component provides a 50-75% attenuation of radiation emitted to a portion of the area of the target plane that is from 5-50% of the total area of the target plane.

In certain embodiments, the shaping component provides a 10-20% attenuation of radiation emitted to a portion of the area of the target plane that is from 10-25% of the total area of the target plane. In certain embodiments, the shaping component provides a 20-50% attenuation of radiation emitted to a portion of the area of the target plane that is from 10-25% of the total area of the target plane. In certain embodiments, the shaping component provides a 30-60% attenuation of radiation emitted to a portion of the area of the target plane that is from 10-25% of the total area of the target plane. In certain embodiments, the shaping component provides a 40-70% attenuation of radiation emitted to a portion of the area of the target plane that is from 10-25% of the total area of the target plane. In certain embodiments, the shaping component provides a 50-75% attenuation of radiation emitted to a portion of the area of the target plane that is from 10-25% of the total area of the target plane.

The present invention is not limited to the aforementioned ranges of attenuation and portions of target planes affected by said attenuation. Table 1 below describes non-limiting examples of embodiments wherein the shaping component attenuates the radiation (by a particular percentage or range of percentages) for a particular portion of the total area of the target plane.

| Example | Amount of Attenuation | Portion of Total Area of Target Plane Affected by the Attenuation |
|---|---|---|
| 1 | 5-20% | 5-25% |
| 2 | 5-20% | 25-50% |
| 3 | 5-20% | 50-75% |
| 4 | 5-20% | 75-90% |
| 5 | 20-40% | 5-25% |
| 6 | 20-40% | 25-50% |
| 7 | 20-40% | 50-75% |
| 8 | 20-40% | 75-90% |
| 9 | 40-75% | 5-25% |
| 10 | 40-75% | 25-50% |
| 11 | 40-75% | 50-75% |
| 12 | 40-75% | 75-90% |
| 13 | 75-90% | 5-25% |
| 14 | 75-90% | 25-50% |
| 15 | 75-90% | 50-75% |
| 16 | 75-90% | 75-90% |

Kits

The present invention also features kits comprising one or more components of the brachytherapy systems of the present invention. For example, in some embodiments, the kit comprises a brachytherapy applicator, e.g., the applicator without the RBS. For example, the kit may comprise the applicator with the handle and a cap system for engaging the handle once the RBS is inside the cap system. In some embodiments, the kit comprises a beta radiation source (e.g., RBS) and a brachytherapy applicator. In some embodiments, the kit comprises a portion of the components of the brachytherapy applicator. In some embodiments, the kit further comprises a radiation attenuation shield.

In some embodiments, the kit comprises a brachytherapy applicator (e.g., the handle portion and the cap system) and an implant for trans-scleral insertion (e.g., an implant for trans-scleral insertion that forms a bleb in the subconjunctival space of the eye (or forms a bleb in the space between the conjunctiva and Tenon's capsule). In some embodiments, the kit comprises a brachytherapy applicator (e.g., the handle portion and the cap system), a radionuclide brachytherapy source, and an implant for trans-scleral insertion (e.g., an implant for trans-scleral insertion that forms a bleb in the subconjunctival space of the eye (or forms a bleb in the space between the conjunctiva and Tenon's capsule). For example, in certain embodiments, the handle and cap are provided in a kit packaged with a MIGS drainage device.

In some embodiments, the kit is for single use. The kit may be provided in sterile packaging.

Methods

The systems and devices of the present invention may be used for a variety of methods. Non-limiting examples of methods of use of the systems and devices herein include methods for applying beta radiation to a target of the eye, for example the site of a bleb formed by a MIGS implant or procedure. Other methods include methods of inhibiting or fibrogenesis or inhibiting or reducing inflammation in a bleb or hole associated with a MIGS implant or procedure, a trabeculectomy, a MIMS procedure, etc.

As an example, the systems and devices of the present invention provide for a method of treating glaucoma drainage procedure conjunctival blebs with a substantially uniform dose of beta therapy, e.g., a substantially uniform dose of beta therapy across a diameter of about 10 mm.

Other methods include methods to maintain the function of a bleb, methods to enhance the function of a MIGS implant, e.g., by maintaining a functional bleb, methods to enhance the success of MIMS, methods for repairing a failed trabeculectomy, methods for repairing a failed MIMS, methods to reduce intraocular pressure (IOP), methods to maintain a healthy IOP, methods for treating glaucoma, etc.

The methods herein comprise applying beta radiation to a target area of the eye. In some embodiments, the target area is a site of the bleb or an expected site of the bleb. (Note that the target is not limited to a bleb or a portion of a bleb.) In some embodiments, the target area surrounds the end of an implant. In some embodiments, the target is from 2 to 5 mm in diameter. In some embodiments, the target is from 5 to 12 mm in diameter. In some embodiments, the target is from 0.3 mm to 0.5 mm in thickness. In some embodiments, the target is from 0.01 mm to 0.7 mm in thickness. In some embodiments, the target is from 0.1 mm to 0.6 mm in thickness. The present invention is not limited to the aforementioned dimensions of the target.

In some embodiments, the method comprises applying the beta radiation prior to a particular surgical procedure, e.g., prior to insertion of a MIGS implant, prior to incision of the conjunctive, prior to creation of a hole associated with MIMS, etc. In some embodiments, the method comprises applying the beta radiation after a particular surgical procedure.

In some embodiments, the methods herein comprise introducing a drug to a site, e.g., a site of the MIGS implant, a site of the bleb, a different part of the eye.

The present invention also features methods for preparing an applicator for emitting beta radiation. In some embodiments, the method comprises inserting a radionuclide brachytherapy source (RBS) into an applicator, e.g., an appropriate place or cavity in the applicator. In some embodiments, the method comprises attaching the RBS to an applicator.

In some embodiments, the systems and devices of the present invention may be used for methods associated with needling procedures, e.g., procedures to the bleb to free or remove scar tissue and/or cystic structures in and/or around the bleb and/or surgery site that may later arise from wound healing or scarring or inflammatory responses to the glaucoma surgery. Needling procedures may affect surgical site morphology, restore the function of the surgery and/or lower the IOP.

Without wishing to limit the present invention to any theory or mechanism, it is believed that treating scar tissue formation on a bleb formed by a trabeculectomy procedure is different from treating a newly-created (and scar tissue-free) bleb at the time of the trabeculectomy. In some embodiments, the methods herein comprise applying beta therapy concomitant with a needling procedure to a bleb formed by a trabeculectomy procedure. In some embodiments, the methods herein comprise applying beta therapy to a trabeculectomy bleb that has formed scar tissue. In some embodiments, the methods herein comprise applying beta therapy to a bleb in the eye of a trabeculectomy patient where the intraocular pressure (IOP) has increased. In some embodiments, the methods herein comprise applying beta therapy to a bleb where the trabeculectomy is failing or has failed. In some embodiments, the methods herein comprise applying beta therapy to a bleb in a second trabeculectomy, where the first trabeculectomy has failed.

In some embodiments, the methods herein comprise applying beta therapy to a bleb that is failing or has failed. In some embodiments, the methods herein comprise applying beta therapy to a MIGS device bleb that is failing or has failed. In some embodiments, the methods herein comprise applying beta therapy to a MIGS device bleb that has formed scar tissue. In some embodiments, the methods herein comprise applying beta therapy to a bleb in the eye of a MIGS device patient where the intraocular pressure (IOP) has increased.

In some embodiments, the methods herein comprise applying another drug in addition to beta radiation to the eye. In some embodiments, the methods herein comprise applying another antimetabolite (e.g., mitomycin-c or 5-fluorouracil) in addition to beta radiation. In some embodiments, the methods comprise administering pharmaceutical eye drops or a liquid anti-metabolite or other liquid drug. In some embodiments, the drug is administered before, during, and/or after a surgical procedure.

The systems and devices (and methods) of the present invention may also be applied to wound healing, e.g., wounds in the eye due to foreign body insertion, trauma, ocular surface wounds, etc. One model of wound healing divides the process into hemostasis, inflammation, proliferation, and remodeling. The first phase of hemostasis begins immediately after wounding, with vascular constriction and fibrin clot formation. The clot and surrounding wound tissue release pro-inflammatory cytokines and growth factors such as transforming growth factor (TGF)-β, platelet-derived growth factor (PDGF), fibroblast growth factor (FGF), and epidermal growth factor (EGF). Once bleeding is controlled, inflammatory cells migrate into the wound and promote the inflammatory phase, which is characterized by the sequential infiltration of neutrophils, macrophages, and lymphocytes. In the early wound, macrophages release cytokines that promote the inflammatory response by recruiting and activating additional leukocytes. As macrophages clear these apoptotic cells, they undergo a phenotypic transition to a reparative state that stimulates keratinocytes, fibroblasts, and angiogenesis to promote tissue regeneration. T-lymphocytes migrate into wounds following the inflammatory cells and macrophages, and peak during the lateproliferative/early-remodeling phase. T-cells regulate many aspects of wound healing, including maintaining tissue integrity, defending against pathogens, and regulating inflammation. The proliferative phase generally follows and overlaps with the inflammatory phase, and is characterized by epithelial proliferation and migration over the provisional matrix within the wound (re-epithelialization). In the reparative dermis, fibroblasts and endothelial cells are the most prominent cell types present and support capillary growth, collagen formation, and the formation of granulation tissue at the site of injury. Within the wound bed, fibroblasts produce collagen as well as glycosaminoglycans and proteoglycans, which are major components of the extracellular matrix (ECM). Following robust proliferation and ECM synthesis, wound healing enters the final remodeling phase, which can last for years.

The radiation attenuation masks of the present invention reduce to acceptable medical practice the use of beta irradiation in trabeculectomy as a competitive first-choice therapy. This may be achieved both by: (1) the beta radiation source output is optimized to the Planning Treatment Volume(s) specific to the trabeculectomy surgical wound and bleb, and (2) minimizing stray dose to the lens, and thus empowering decreases in the side effects of induced cataract that otherwise limits selection of this treatment modality.

Of note, by convention dose variation is described as that across the diameter assuming a central point maximum dose. However, in practice it has been demonstrated that the maximum dose may be off center. Thus, the description of dose across the diameter may also include the variation of dose over the area.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A brachytherapy system for applying a dose of beta radiation to a target, said brachytherapy system comprising:
   (a) a handle having a distal end; and
   (b) a cap system attachable to the distal end of the handle, the cap system comprises:
      (i) a cylindrical base ring having a first end and a second end opposite the first end and an inner cavity therein for accepting a radionuclide brachytherapy source (RBS), the first end is open to allow for insertion of the RBS into the inner cavity; and
      (ii) a barrier surface sealing the second end of the base ring so as to prevent passing of the RBS through the second end; and a shaping component disposed on an interior surface of the barrier surface in the inner cavity of the base ring, the shaping component is shaped and constructed to regulate a dose of beta radiation delivered from the RBS to a target plane of a treatment area.

2. The system of claim 1, wherein the barrier surface is constructed from a material comprising a synthetic polymer material.

3. The system of claim 1, wherein the base ring is constructed from a material comprising a metal, metal alloy, plastic, or a combination thereof.

4. The system of claim 1, wherein the inner cavity of the base ring is 11 mm in diameter.

5. The system of claim 1, wherein the shaping component is dome shaped, rectangular, a round disk, or an annulus.

6. The system of claim 1, wherein the shaping component is a combination of two or more pieces.

7. The system of claim 6, wherein the combination of two or more pieces comprises pieces constructed from different materials.

8. The system of claim 1, wherein the shaping component is constructed from a material comprising one or a combination of: stainless steel, titanium, copper, brass, tungsten, tungsten-copper, a metal alloy, or a polymer.

9. The system of claim 1, wherein the cap system and the handle attach via a threaded mechanism.

10. The system of claim 9, wherein threads are disposed on the base ring at the first end that engage threads disposed on the distal end of the handle.

11. The system of claim 1, wherein the cap system attaches to the distal end of the handle via a snap mechanism.

12. The system of claim 1 further comprising the RBS housed in the inner cavity of the base ring.

13. The system of claim 12, wherein the RBS comprises Strontium-90 in secular equilibrium with Yttrium-90.

14. A brachytherapy system for applying a dose of beta radiation to a target, said brachytherapy system comprising:
   (a) a handle having a distal end; and
   (b) a cap system attachable to the distal end of the handle, the cap system comprises:
      (i) a cylindrical base ring having a first end and a second end opposite the first end and an inner cavity therein for accepting a radionuclide brachytherapy source (RBS), the first end is open to allow for insertion of the RBS into the inner cavity; and
      (ii) a barrier surface sealing the second end of the base ring so as to prevent passing of the RBS through the second end; and a shaping component disposed on an interior surface of the barrier surface in the inner cavity of the base ring, the shaping component is shaped and constructed to regulate a dose of beta radiation delivered from the RBS to a target plane of a treatment area;

wherein cap threads are disposed on the cylindrical base ring at the first end and handle threads are disposed on the distal end of the handle, wherein the cap threads are configured to temporarily engage the handle threads to secure the cap to the handle.

15. The system of claim 14, wherein the shaping component is dome shaped, rectangular, a round disk, or an annulus.

16. The system of claim 14, wherein the shaping component is a combination of two or more pieces.

17. A brachytherapy system for applying a dose of beta radiation to a target, said brachytherapy system comprising:

(a) a handle having a distal end; and (b) a cap system attachable to the distal end of the handle, the cap system comprises:

(i) a cylindrical base ring having a first end and a second end opposite the first end and an inner cavity therein for accepting a radionuclide brachytherapy source (RBS), the first end is open to allow for insertion of the RBS into the inner cavity; and (ii) a barrier surface sealing the second end of the base ring so as to prevent passing of the RBS through the second end; and a shaping component disposed on an interior surface of the barrier surface in the inner cavity of the base ring, the shaping component is shaped and constructed to regulate a dose of beta radiation delivered from the RBS to a target plane of a treatment area;

wherein the cap further comprises a tab that extends from the first end of the cylindrical base ring and the handle further comprises a tab lock adapted to accept the tab of the cap to secure the cap to the handle.

18. The system of claim 17, wherein the shaping component is dome shaped, rectangular, a round disk, or an annulus.

19. The system of claim 17, wherein the shaping component is a combination of two or more pieces.

20. The system of claim 17, wherein the tab is a pair of opposing tabs and the tab lock is a pair of opposing tab locks, wherein the pair of opposing tabs are adapted to engage the pair of opposing tab locks.

\* \* \* \* \*